(12) United States Patent
Yang et al.

(10) Patent No.: US 12,599,380 B2
(45) Date of Patent: Apr. 14, 2026

(54) SURGICAL STAPLER AND STAPLE CARTRIDGE FOR THE SAME

(71) Applicant: Cilag GmbH International, Zug (CH)

(72) Inventors: Mengli Yang, Shanghai (CN); Hong Xiangchun, Shanghai (CN); Junjie Wang, Xuhui (CN); Chunchun Liu, Shanghai (CN); Sheng Ding, Xuhui (CN)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/851,247

(22) PCT Filed: Apr. 5, 2023

(86) PCT No.: PCT/IB2023/053476
§ 371 (c)(1),
(2) Date: Sep. 26, 2024

(87) PCT Pub. No.: WO2023/194931
PCT Pub. Date: Oct. 12, 2023

(65) Prior Publication Data
US 2025/0195065 A1 Jun. 19, 2025

(30) Foreign Application Priority Data
Apr. 8, 2022 (CN) .......................... 202210370116.9

(51) Int. Cl.
*A61B 17/072* (2006.01)
(52) U.S. Cl.
CPC .. *A61B 17/072* (2013.01); *A61B 2017/07264* (2013.01); *A61B 2017/07271* (2013.01)
(58) Field of Classification Search
CPC .................................................. A61B 17/072
See application file for complete search history.

(56) References Cited

U.S. PATENT DOCUMENTS 4,354,628 A 10/1982 Green
4,527,724 A * 7/1985 Chow .................. A61B 17/072
227/19

(Continued)

FOREIGN PATENT DOCUMENTS

CN 102835983 B 8/2016
EP 0537572 A2 4/1993

(Continued)

OTHER PUBLICATIONS

International Search report and Written Opinion dated Jul. 21, 2023, for International Application No. PCT/IB2023/053476, 9 pages.

(Continued)

*Primary Examiner* — Nathaniel C Chukwurah
(74) *Attorney, Agent, or Firm* — FBT Gibbons LLP

(57) ABSTRACT

A cartridge body of a staple cartridge includes a tissue contact platform; a plurality of staple cavities; and a retaining pin assembly slidably arranged in an end of the cartridge body proximate to the outside. In the longitudinal direction of the staple cartridge, an outermost edge of an outermost staple cavity in at least one row of the staple cavities is aligned with or extends beyond a longitudinal axis of the pin rod. The A surgical stapler includes an anvil for causing staples in the staple cartridge formed and an anvil side retaining pin receiving hole for receiving a free end of a retaining pin assembly of the staple cartridge. An outermost edge of an outermost staple forming pocket in at least one row of the staple forming pockets is aligned with or extends beyond a center of the retaining pin receiving hole at the anvil side.

20 Claims, 18 Drawing Sheets

(56)                    References Cited

U.S. PATENT DOCUMENTS

| | | | |
|---|---|---|---|
| 4,568,009 A | 2/1986 | Green | |
| 4,573,622 A | 3/1986 | Green et al. | |
| 4,585,153 A | 4/1986 | Failla | |
| 4,715,520 A | 12/1987 | Roehr et al. | |
| 4,805,823 A * | 2/1989 | Rothfuss | A61B 17/072 227/139 |
| 4,848,637 A * | 7/1989 | Pruitt | A61B 17/072 227/19 |
| 4,930,503 A * | 6/1990 | Pruitt | A61B 17/072 227/19 |
| 5,439,155 A | 8/1995 | Viola | |
| 5,462,215 A | 10/1995 | Viola et al. | |
| 5,547,117 A | 8/1996 | Hamblin et al. | |
| 5,641,111 A | 6/1997 | Ahrens et al. | |
| 5,810,240 A | 9/1998 | Robertson | |
| 5,919,198 A | 7/1999 | Graves et al. | |
| 6,805,273 B2 * | 10/2004 | Bilotti | A61B 17/115 227/176.1 |
| 6,817,508 B1 | 11/2004 | Racenet et al. | |
| 8,328,064 B2 | 12/2012 | Racenet et al. | |
| 11,202,628 B2 | 12/2021 | Posey et al. | |
| 2004/0084505 A1 | 5/2004 | Bilotti et al. | |
| 2005/0139629 A1 | 6/2005 | Schwemberger et al. | |
| 2011/0226837 A1 | 9/2011 | Baxter, III et al. | |
| 2013/0206813 A1 | 8/2013 | Nalagatla | |
| 2015/0119904 A1 | 4/2015 | Ji et al. | |
| 2017/0281177 A1 | 10/2017 | Harris et al. | |
| 2020/0205810 A1 | 7/2020 | Posey et al. | |
| 2020/0205811 A1 | 7/2020 | Posey et al. | |
| 2020/0337699 A1 | 10/2020 | Rector et al. | |
| 2020/0337700 A1 | 10/2020 | Hontz et al. | |
| 2021/0186495 A1 | 6/2021 | Shelton, IV et al. | |
| 2022/0000479 A1 | 1/2022 | Shelton, IV et al. | |
| 2022/0142641 A1 | 5/2022 | Wang | |
| 2024/0225642 A1 | 7/2024 | Ren et al. | |
| 2025/0049436 A1 | 2/2025 | Wang | |
| 2025/0204912 A1 | 6/2025 | Yang et al. | |
| 2025/0213248 A1 | 7/2025 | Zhang et al. | |
| 2025/0213250 A1 | 7/2025 | Ding et al. | |
| 2025/0228559 A1 | 7/2025 | Ding et al. | |
| 2025/0255605 A1 | 8/2025 | Yang et al. | |

FOREIGN PATENT DOCUMENTS

| | | |
|---|---|---|
| EP | 0537572 B1 | 6/1999 |
| EP | 1550411 A1 | 7/2005 |
| EP | 1552791 A1 | 7/2005 |
| EP | 1552791 B1 | 6/2009 |
| EP | 1550411 B1 | 7/2009 |
| EP | 3225179 A1 | 10/2017 |
| EP | 3476310 A1 | 5/2019 |
| EP | 3225179 B1 | 4/2020 |
| EP | 3636166 A2 | 4/2020 |
| EP | 3673826 A1 | 7/2020 |
| EP | 3730068 A1 | 10/2020 |
| EP | 3730070 A1 | 10/2020 |
| EP | 3730069 B1 | 7/2023 |
| EP | 3730068 B1 | 9/2023 |
| EP | 3636166 B1 | 3/2024 |
| WO | 2021/168704 A1 | 9/2021 |
| WO | 2021/168726 A1 | 9/2021 |

OTHER PUBLICATIONS

International Search Report and Written Opinion dated Jul. 4, 2023 for Application No. PCT/IB2023/053467, 9 pages.
International Search Report and Written Opinion dated Jul. 12, 2023 for Application No. PCT/IB2023/053469, 9 pages.
International Search Report and Written Opinion dated Jun. 29, 2023 for Application No. PCT/IB2023/053477, 10 pages.
International Search Report and Written Opinion dated Jul. 5, 2023 for Application No. PCT/IB2023/053478, 9 pages.
International Search Report and Written Opinion dated Jul. 5, 2023 for Application No. PCT/IB2023/053481, 10 pages.
International Search Report and Written Opinion dated Jul. 14, 2023 for Application No. PCT/IB2023/053483, 12 pages.

* cited by examiner

SURGICAL STAPLER AND STAPLE CARTRIDGE FOR THE SAME

TECHNICAL FIELD

The present disclosure relates to a field of medical staplers or severing staplers, and more specifically relates to a surgical stapler for stapling tissue in an open surgical procedure and a staple cartridge for use with the surgical stapler.

BACKGROUND

In the prior art, a medical stapler or medical severing stapler (hereinafter collectively referred to as surgical stapler) is typically used to apply multiple rows of staplers on opposing sides of an incision formed in tissue during a surgical procedure, so as to suture the incision and thus reduce or eliminate tissue bleeding and accelerate wound healing. The typical surgical stapler adapted to open surgery has an end effector disposed at the distal end of the surgical stapler, and the end effector includes a staple cartridge for receiving staples and an anvil for stapling-deforming the staples disposed opposite the staple cartridge, where the anvil and the staple cartridge jointly form a jaw structure to clamp tissue.

In order to maintain a stable relative positional relation among the staple cartridge, anvil and tissue to be stapled throughout the process where the surgical stapler clamps the tissue until the stapling is completed, a retaining pin is often provided in the cartridge body of the staple cartridge. The retaining pin is used to cause the staple cartridge aligned with the anvil and fixed when the end effector clamps the tissue to be stapled, such that the staple forming pockets in the anvil are aligned with the staple cavity openings in the staple cartridge, to prevent a relative movement between the staple cartridge and the anvil resulting from an external force applied upon firing of the surgical stapler. In the case, the staples cannot be accurately aligned with the staple forming pockets formed on the anvil, such that the staples cannot successfully deform and thus lead to a failure to effectively staple the tissue.

In the existing open surgical stapler, the retaining pin is generally centered relative to the longitudinal centerline of the staple cartridge, and the staple cavity openings are disposed at both sides of the centerline along the longitudinal direction of the staple cartridge, as shown in FIG. 1. In such an arrangement, the retaining pin chute opening is arranged further outside relative to the outermost staple cavity opening. Such arrangement has a disadvantage that, since the stapling line formed by the outermost staple cannot cover the area where the retaining pin chute opening is located during stapling, a clearance is formed therebetween. In particular when the area of the tissue to be stapled has a large width, the width of the tissue to be stapled exceeds the respective lengths of the staple cartridge and the anvil of the stapler. In the circumstance, the retaining pin may squeeze or even penetrate the tissue when the tissue is clamped, such that the staples cannot cover the tissue around the retaining pin, leaving a gap formed in the area not covered by the staple lines. This probably leads to local bleeding and tissue fluid leakage, delays healing of the incision, prolongs the hemostasis time and causes other undesirable symptoms, such as local inflammation and the like. Sometimes, a clinician even needs to perform an extra local stapling and hemostatic operation, thus prolonging the actual surgery and recovery time.

In order to solve the above-mentioned problems, there is a need for a novel open surgical stapler that can allow the outermost stapling line to cover at least a half of the retaining pin chute opening, to ensure the tissue stapling effect and thus reduce the risks of bleeding and tissue fluid leakage.

SUMMARY

According to an aspect of the present disclosure, there is provided a staple cartridge for use with a surgical stapler, comprising: a plurality of staples; and a cartridge body, comprising: a tissue contact platform; a plurality of staple cavities, wherein each of the staple cavities comprises an opening formed in the tissue contact platform, the staples positioned in each of the staple cavities and extending out of the opening when deployed, and wherein the plurality of staple cavities are arranged in rows along a longitudinal direction of the staple cartridge; and a retaining pin assembly slidably disposed in an end of the cartridge body proximate to the outside and operably connected to a closure drive mechanism of the surgical stapler, such that the retaining pin assembly can extend distally out of a retaining pin hole opened on the tissue contact platform along a longitudinal direction of the surgical stapler when the closure drive mechanism is actuated, wherein the retaining pin assembly comprises a cylindrical pin rod extending along a longitudinal direction of the retaining pin assembly; wherein, in the longitudinal direction of the staple cartridge, an outermost edge of an outermost staple cavity in at least one row of the staple cavities is aligned with or extends beyond a longitudinal axis of the pin rod; and wherein the retaining pin assembly is offset relative to a longitudinal centerline of the staple cartridge; or alternatively the retaining pin assembly is centered relative to the longitudinal centerline of the staple cartridge while a longitudinal centerline of a plurality of rows of the staple cavities is offset relative to the longitudinal centerline of the staple cartridge.

According to the above-mentioned technical solution of the present disclosure, irrespective of the number of rows of staples in the staple cartridge and irrespective of the longitudinal centerline of the stapling lines being offset from the longitudinal centerline of the staple cartridge, at least one staple cavity opening in at least one row of staple cavity openings, preferably a plurality of staple cavity openings, can extend to or pass through the center of the pin rod (namely the center of the retaining pin hole for receiving the pin rod of the retaining pin assembly), to cover the area around the retaining pin hole and thus avoid the situation where no staples are applied around the retaining pin hole in the stapling procedure. In this way, the technical solution can reduce the possibility of local bleeding and tissue fluid leakage and enhance the stapling effect.

In addition, the staple cartridge according to the present disclosure includes a pin rod with a complete circular cross section having a greater diameter. As compared with the semi-circular pin rod according to the prior art, the pin rod according to the present invention cannot only be enhanced in strength but also can significantly improve the stability of the retaining pin assembly during operation, thereby guaranteeing the formed staple quality.

According to a preferred implementation of the present disclosure, the pin rod of the retaining pin assembly is offset relative to the longitudinal centerline of the staple cartridge, and the longitudinal centerline of the plurality of rows of the staple cavities coincides with the longitudinal centerline of the staple cartridge.

According to another preferred implementation of the present disclosure, the pin rod of the retaining pin assembly is offset relative to the longitudinal centerline of the staple cartridge, and the longitudinal centerline of the plurality of rows of the staple cavities is offset relative to the longitudinal centerline of the staple cartridge.

According to a further preferred implementation of the present disclosure, the staple cavities are arranged in two rows, where an outermost edge of an outermost staple cavity in one of the two staple cavity rows extends beyond the longitudinal axis of the pin rod of the retaining pin assembly, and another staple cavity row is positioned adjacent to the retaining pin hole.

According to a still further preferred implementation of the present disclosure, the pin rod comprises a free end that can extend out of the retaining pin hole and the other end opposing the free end, and the retaining pin assembly further comprises: a pin base fixedly connected to the other end of the pin rod, wherein the pin rod is offset relative to a longitudinal center axis of the pin base. Such arrangement can be applied in cooperation with the solution of offsetting the retaining pin rod, which is helpful to cause the pin rod of the retaining pin assembly to pass through the structure of the staple driver plate such that the retaining pin assembly can be pushed through the staple driver plate to reach a more distant position. In this way, the present disclosure can save the inner space of the staple cartridge and reduce the height of the staple cartridge.

According to a still further preferred implementation of the present disclosure, the retaining pin assembly has an asymmetric structure at two sides of the offset pin rod. In the case, by employing an asymmetric arrangement at a side to which the pin rod is offset, for example, by increasing the volume at the offset side, the present disclosure can increase the support strength of the offset pin rod and thus guarantee the stability of the offset retaining pin assembly in a telescopic process.

According to a still further preferred implementation of the present disclosure, the staple cartridge further comprises a staple driver plate extending along the longitudinal direction of the staple cartridge and provided, on a surface facing a distal end of the surgical stapler, with a plurality of teeth extending towards a distal end of the surgical stapler and configured to push the staples out of the staple cavities, wherein the staple driver plate is formed at a distal end portion proximate to the retaining pin assembly with an avoidance feature that allows the retaining pin assembly to advance towards the distal end of the surgical stapler by surpassing the staple driver plate.

According to a still further preferred implementation of the present disclosure, the avoidance feature is a cutout formed at one side of the staple driver plate adjacent to the retaining pin assembly, the cutout extends along a firing direction of the staple cartridge, and is configured to allow the retaining pin to pass therethrough. In this way, the present disclosure cannot only accomplish the objective of allowing the retaining pin assembly to pass but only can ensure that at least one row of staple lines is formed around the retaining pin assembly, thereby reducing bleeding and leakage.

According to a still further preferred implementation of the present disclosure, the retaining pin assembly further comprises clips formed at both sides of the pin base, and the clips are configured to extend out of the cartridge body along slots formed on two side surfaces of the cartridge body and extending along a firing direction of the staple cartridge so that the retaining pin assembly is operated by a user to slide along the slots.

According to a still further preferred implementation of the present disclosure, the clips have an ear-like structure, to facilitate a user to manually operate the surgical stapling instrument.

According to a still further preferred implementation of the present disclosure, the ear-like clips located at two sides of the pin base are different in size. This is an optimized adjustment to the arrangement where the pin rod of the retaining pin assembly is offset, to guarantee the stability of the offset retaining pin assembly in a telescopic process and thus ensure the staple forming quality.

According to a still further preferred implementation of the present disclosure, the cartridge body further comprises a plurality of ridges extending from the tissue contact platform, and wherein at least a part of each of the staple cavity openings is surrounded by portions of the ridges or a portion of a ridge. With the structure, the ridges can first contact the tissue when the jaws are closed, to prevent or at least restrict a relative movement between the tissue and the staple cartridge.

In addition, according to a still further preferred implementation of the present disclosure, a bump is formed around at least a part of the retaining pin hole. With such structure, a better guidance can be provided to the pin rod upon actuation of the retaining pin assembly, and the tissue can be prevented from being squeezed out when the end effector is closed.

According to a still further preferred implementation of the present disclosure, a free end of the retaining pin assembly is configured as a tip, such that the retaining pin assembly can conveniently penetrate the tissue and be smoothly inserted into the retaining pin receiving hole at the anvil side.

According to a still further preferred implementation of the present disclosure, the pin rod of the retaining pin assembly has a diameter greater than 1.7 mm. As such, the present disclosure cannot only ensure a sufficient strength of the pin rod but also can guarantee that the pin rod is sufficiently stable when penetrating the tissue.

According to another aspect of the present disclosure, there is provided a surgical stapler for stapling tissue in a surgical procedure, comprising: a staple cartridge according to various preferred implementations of the present disclosure; an anvil for forming staples in the staple cartridge; and a firing drive mechanism operably connected to the staple cartridge, the staple firing mechanism for actuating the staple driver plate to drive a plurality of staple drivers to move distally from the surgical stapler, so as to deploy the staples from the staple cavities, wherein the anvil comprises: a tissue contact surface; a plurality of staple forming pockets formed on the tissue contact surface, the staple forming pockets arranged in rows corresponding to a plurality of staple cavities of the staple cartridge; and a retaining pin receiving hole for receiving a free end of a retaining pin assembly of the staple cartridge, wherein the retaining pin receiving hole arranged at an end of the anvil proximate to the outside, wherein, in a longitudinal direction of the anvil, an outermost edge of an outermost staple forming pocket in at least one row of the staple forming pockets is aligned with or extends beyond a center of the retaining pin receiving hole at the anvil side.

According to the above implementation solution of the present disclosure, the anvil employs an arrangement consistent with the staple cartridge such that at least one row of stapling lines can extend to or pass through a center of a retaining pin hole for receiving the pin rod, so as to cover the area around the retaining pin and thus avoid the situation that no staples are applied around the retaining pin hole.

According to a preferred implementation of the present disclosure, the retaining pin receiving hole at the anvil side is centered relative to a longitudinal centerline of the anvil, and a longitudinal centerline of a plurality of rows of the staple forming pockets is offset relative to the longitudinal centerline of the anvil.

According to another preferred implementation of the present disclosure, the retaining pin receiving hole at the anvil side is offset relative to the longitudinal centerline of the anvil, and a longitudinal centerline of a plurality of rows of the staple forming pockets is offset relative to the longitudinal centerline of the anvil.

According to a further preferred implementation of the present disclosure, the retaining pin receiving hole at the anvil side is offset relative to the longitudinal centerline of the anvil, and a longitudinal centerline of a plurality of rows of the staple forming pockets coincides with the longitudinal centerline of the anvil.

According to a still further preferred implementation of the present disclosure, the retaining pin receiving hole at the anvil side is opened outside towards a side surface of the anvil along a transverse direction of the anvil. With such design, the present disclosure can facilitate the position adjustment of the retaining pin assembly when the surgical stapler is closed.

According to a still further preferred implementation of the present disclosure, the retaining pin receiving hole at the anvil side connects to the outside via a notch formed on an edge of the anvil at one side proximate to the retaining pin receiving hole.

According to a still further preferred implementation of the present disclosure, the anvil comprises a first portion and a second portion divided along a median plane of the surgical stapler, the retaining pin receiving hole at the anvil side being disposed on the first portion, and wherein a width of the first portion is greater than a width of the second portion.

According to a still further preferred implementation of the present disclosure, the surgical stapler further comprises an anvil mounting portion on which the anvil is fixedly mounted, wherein the anvil mounting portion is provided on a side surface with a thin inner shim so that a median plane of the anvil is caused to offset relative to a median plane of the surgical stapler. With such structure, the present disclosure can enhance the strength of the distal end of the surgical stapler, thus absorbing an operating force applied at the distal end and preventing damage to the clamped tissue. It is advantageous in particular when the retaining pin assembly has a thick pin rod, which cannot only ensure a good staple forming effect in the end but can also reduce impact or damage to the tissue.

According to another preferred implementation of the present disclosure, a shape of the inner shim is the same as a shape of at least a part of the side surface of the anvil mounting portion.

The staple cartridge and surgical stapler according to the present disclosure can solve the above-mentioned technical problems existing in the prior art, which cannot only ensure the tissue stapling effect, thereby reducing the risks of bleeding and tissue fluid leakage, but also can optimize the inner space of the staple cartridge, thereby reducing the height of the staple cartridge. In addition, by disposing a thin inner shim on a side surface of the anvil mounting portion, impact or damage to the tissue can be reduced.

BRIEF DESCRIPTION OF THE DRAWINGS

Preferred embodiments of the present disclosure will be described below in detail with reference to the accompanied drawings. The description below is provided merely as an example, rather than suggesting any limitations to the present disclosure, and other similar situations that the objectives of the present disclosure can also be accomplished all fall into the protection scope of the present disclosure. For ease of understanding, the same reference signs are employed for the same components (in either of the prior art and the various implementations of the present disclosure) throughout the description and drawings. In the drawings:

FIG. 9a is a view according to the prior art, and FIG. 9b is a view according to a preferred embodiment of the present disclosure;

DETAILED DESCRIPTION OF EMBODIMENTS

Figure 1:
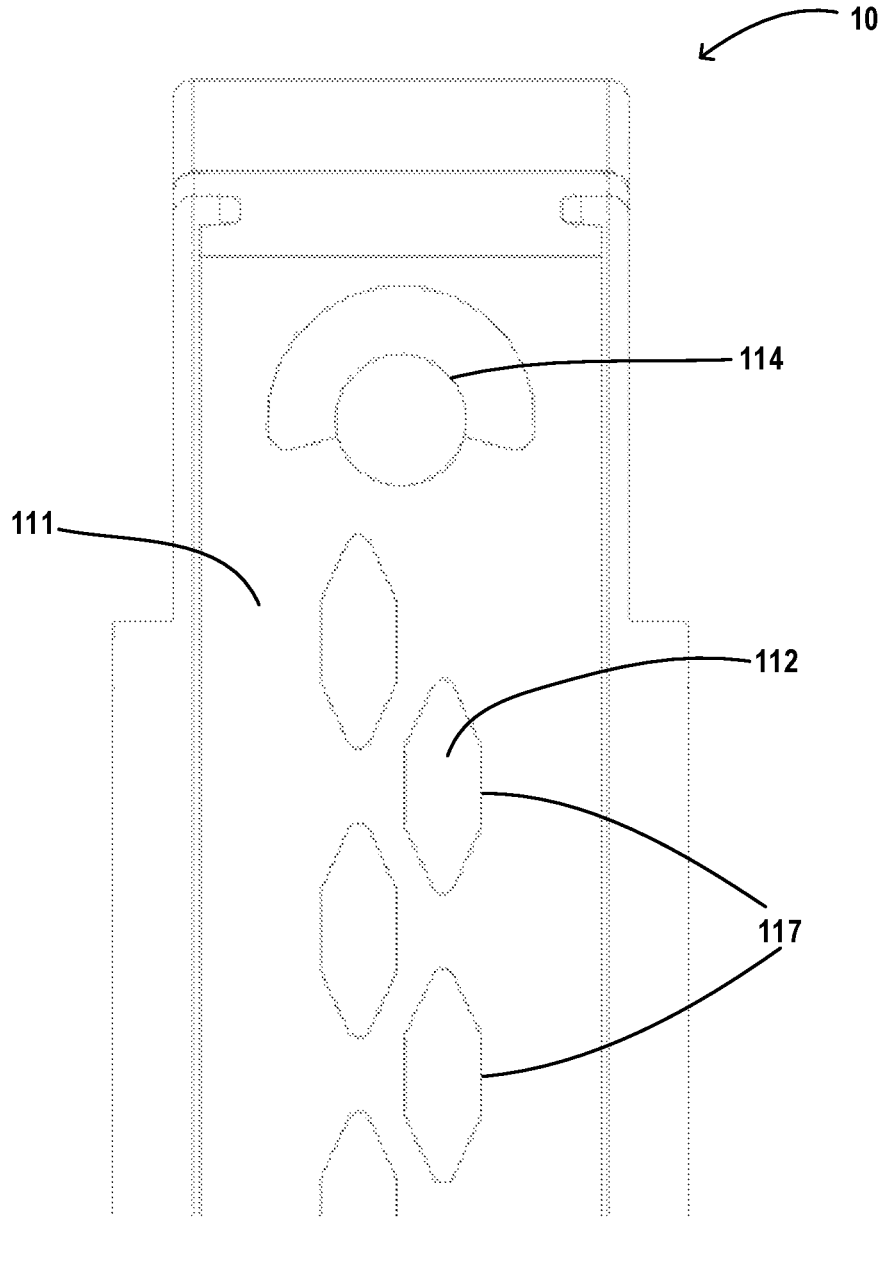
FIG. 1 is a schematic view of a staple cartridge according to the prior art, which shows relative positions of a retaining pin hole on a tissue contact platform and a staple cavity opening.

With reference to the drawings, the technical solution of the present disclosure will be further described below through specific embodiments but not confined to those embodiments. It would be appreciated that the embodiments described and illustrated herein are non-limiting examples, and the specific structural and functional details disclosed herein may be representative and illustrative. Variations and changes thereto may be made without departing from the scope of the claims.

As used here, "various embodiments," "some embodiments," "an embodiment," "embodiment" or the like refer to that specific features, structures or characteristics described with reference to the embodiment(s) are included in at least one embodiment, and therefore does not necessarily indicate the same embodiment. In addition, in one or more embodiments, the specific features, structure or characteristics may be combined in any appropriate manners. Accordingly, without limitation, specific features, structures or characteristics shown or described with reference to one embodiment may be entirely or partly combined with features, structures or characteristics included in one or more other embodiments.

The terms "proximal," "distal," "proximal end" and "distal end" are used herein with reference to a user or operator manipulating the surgical stapler, where "proximal" and "proximal end" refer to the side closest to the operator, and "distal" and "distal end" refer to the side located away from the operator. For example, the end effector is located at a distal end with reference to a surgeon manipulating the surgical stapler handle.

For the terms "inner" and "outer" as used herein, with respect to the longitudinal extending axis line of the staple cartridge or anvil, an inner side refers to a side proximate to the hook plate extending towards the distal end of the surgical stapler, and a distal side refers to a side located away from the hook plate. The longitudinal extending direction of the staple cartridge or anvil is perpendicular to the longitudinal extending direction of the surgical stapler.

As used herein, the term "length" related to the staple cartridge refers to a dimension of the staple cartridge along its longitudinal extending direction; "width" refers to a dimension in a direction perpendicular to the length direction of the staple cartridge in a plane parallel to the tissue contact platform of the staple cartridge; and "height" refers to a dimension along the longitudinal extension direction of the surgical stapler.

In addition, the terms "transverse direction," "longitudinal direction" and "vertical direction" are used herein with reference to the structure of the staple cartridge or anvil described, where a longitudinal direction refers to a length direction of the staple cartridge or anvil, a transverse direction refers to a width direction of the staple cartridge or anvil, and a vertical direction refers to a height direction of the staple cartridge or anvil.

It would be appreciated that, for brevity and clarity, spatial terms such as "vertical," "horizontal," "up," and "down" may be used herein with reference to the embodiments as shown. However, those terms are provided to assist the reader, rather than indented to be limiting and absolute.

Moreover, although the embodiments shown in the drawings only relate to a linear stapler adapted to open surgery, the protection scope of the present disclosure should not be thereto, which may further cover a surgical stapler with an angled head. Besides, the protection scope of the stapler according to the present disclosure should not be restricted to surgical staplers only having a stapling function as described here, but instead should cover surgical severing staplers having both severing and stapling functions. That is, the surgical instrument is also provided with a severing blade, which is a surgical stapler that can simultaneously implement the severing and stapling functions.

For example, the Chinese patent CN102835983B describes a surgical stapler adapted to open surgery, comprising a support base, a trigger located at a proximal end, a handle and a retaining pin, where the retaining pin is operatively connected to and extends distally from the support base. The support base at the upper part supports the retaining pin, and the retaining pin extends through a through hole at the upper end of the movable jaw, and the retaining pin can be advanced to the hole in the anvil to guarantee correct alignment between the anvil and the staple cartridge and retain the tissue captured therebetween. If the retaining pin moves distally and is not in situ, the trigger of the surgical stapler cannot be fired. The trigger can be triggered only when the operator pushes the retaining pin in situ according to the needs.

The present disclosure relates to a surgical stapler having similar configuration and functions and adapted to open surgery.

Figure 2:
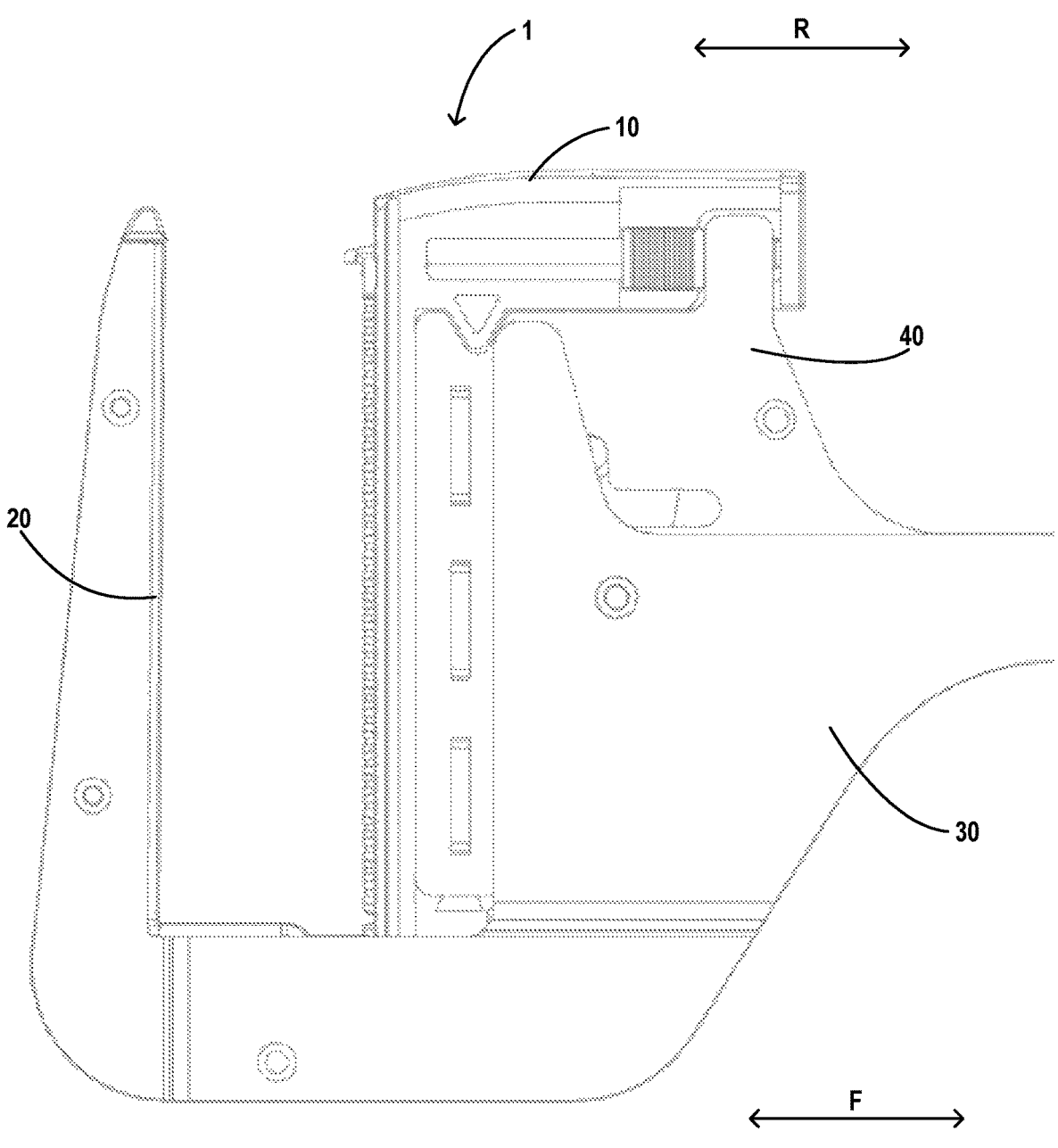
FIG. 2 is a side view of an end effector of a surgical stapler according to the present disclosure.

Hereinafter, reference will be made to FIG. 2 to describe the basic structure of the surgical stapler according to the present disclosure. FIG. 2 schematically illustrates a part of an end effector 1 of the surgical stapler according to the present disclosure. For convenience, only the structure related to the technical solution claimed herein is shown, and structures of components, such as a grip, firing mechanism, actuation mechanism and the like, are omitted. For those structures not shown therein, reference may be made to the related description about the prior art.

As shown in FIG. 2, the surgical stapler according to the present disclosure at the distal end is configured with an end effector 1 for clamping tissue to be stapled and implementing a stapling operation. The end effector 1 mainly includes a fixed jaw of a substantially U shape and a movable jaw movable relative to the fixed jaw, where the movable jaw includes a staple cartridge 10 for receiving staples, an anvil 20 is fixedly mounted on the surface of the fixed jaw facing the movable jaw, and the anvil 20 is disposed opposite the staple cartridge 10. The staple cartridge 10 and the anvil 20 jointly form a jaw structure to clamp tissue.

Figure 3:
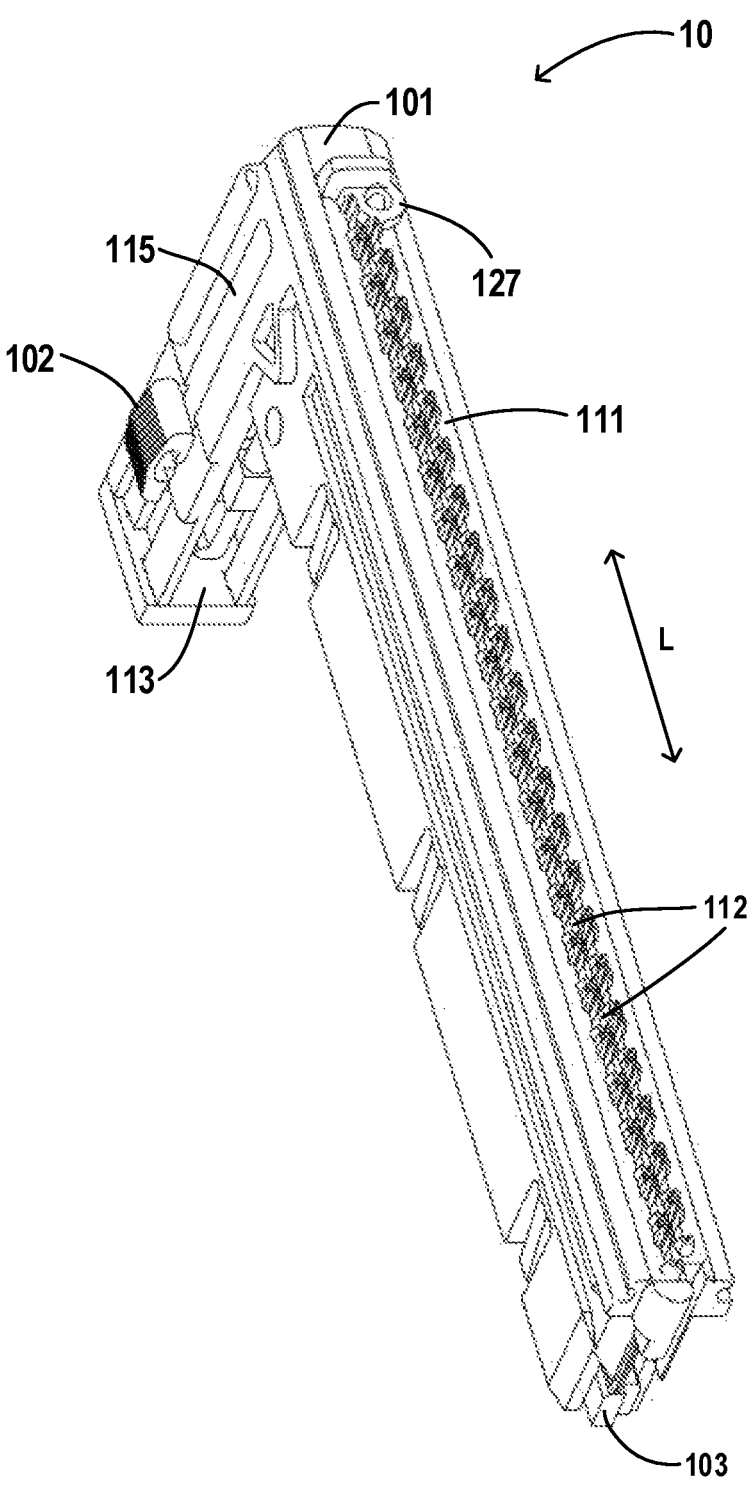
FIG. 3 is a perspective view of a staple cartridge according to the present disclosure.

The staple cartridge 10 is a replaceable, disposable product, which can be replaced by the surgeon with a new one after each firing operation has been completed. As shown in FIG. 3, the staple cartridge 10 mainly includes a plurality of staples and a cartridge body 101, where the cartridge body 101 includes a tissue contact platform 111 extending along the longitudinal direction L of the staple cartridge 10 and a plurality of staple cavities 112 each including an opening 117 located on the tissue contact platform 111, and the plurality of staples are located in each staple cavity 112 and can extend out of the opening 117 when deployed. In addition, the plurality of staple cavities 112 are arranged in two or more rows along the longitudinal direction of the staple cartridge.

Figure 5:
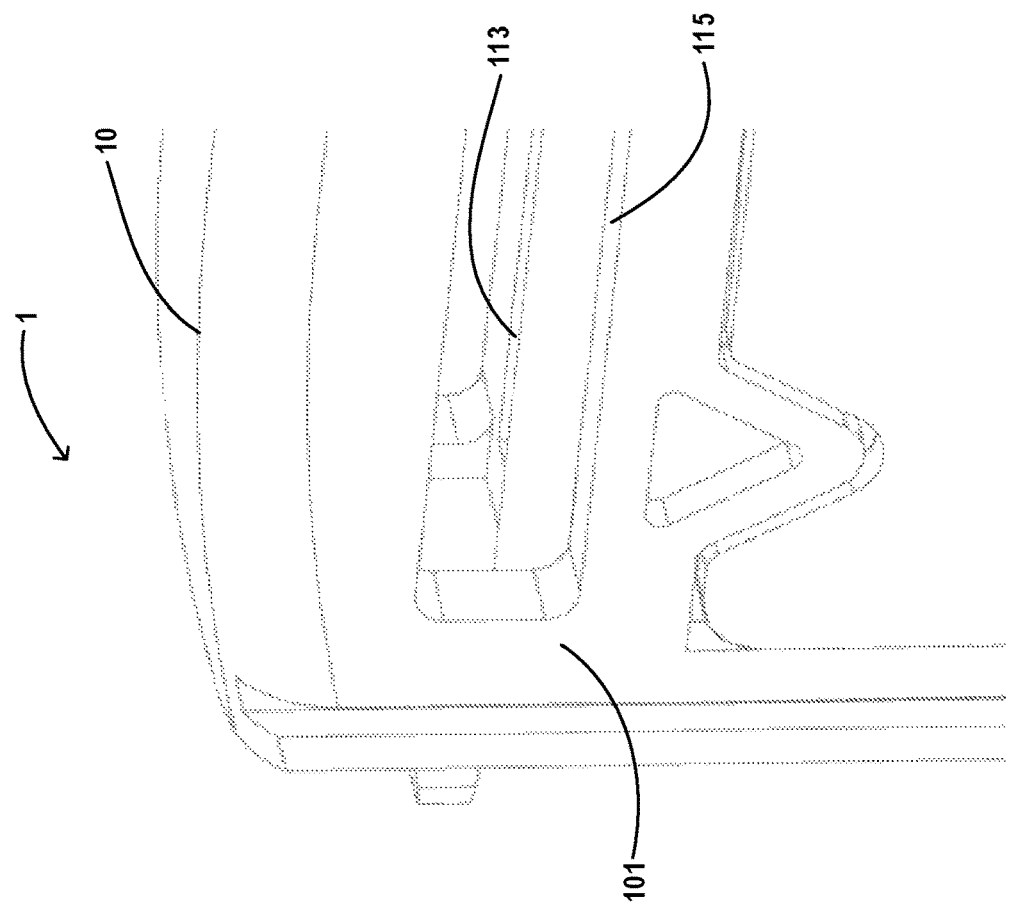
FIG. 5 is a perspective view illustrating a part of an end effector of a surgical stapler according to the present disclosure.
Figure 5:
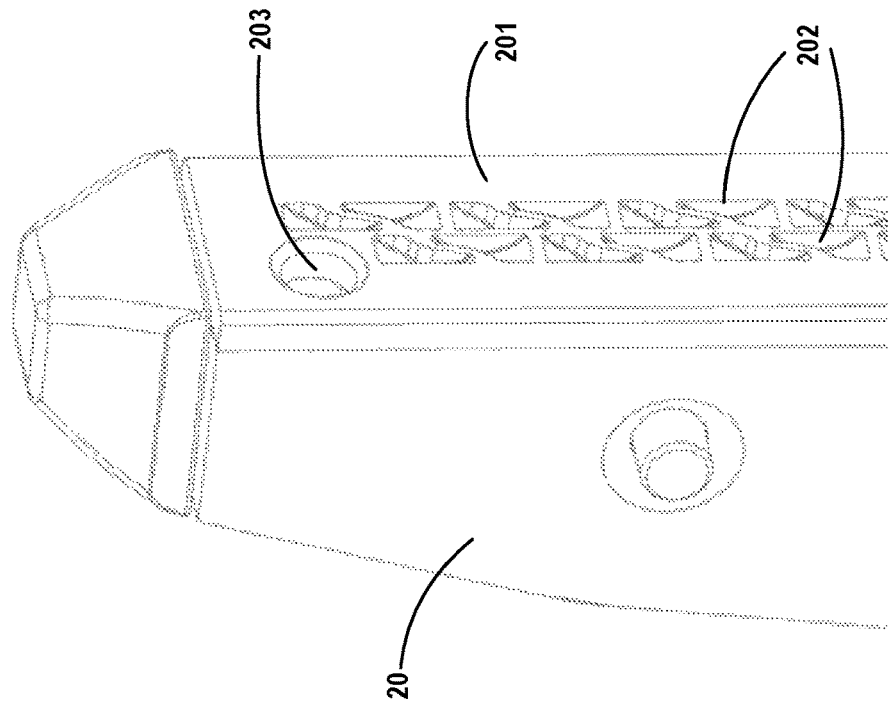

As shown in FIG. 5, the anvil 20 is formed thereon with a plurality of staple forming pockets 202 for stapling-deforming the staples, which are arranged corresponding to the plurality of staple cavities 112 located on the staple cartridge. In addition, as shown in FIG. 2, the anvil 20 is configured integrally with a main body frame 30 of the surgical stapler and fixedly connected to a pistol grip of a closure and fire mechanism of the stapler.

The staple cartridge 10 is received within the main body frame 30 and coupled to a firing drive mechanism also received in the main body frame. The firing drive mechanism is configured to actuate a staple driver plate 103 of the staple cartridge 10 to drive a plurality of staple drivers (i.e., a plurality of teeth on the staple push plate) towards the distal end of the surgical stapler 1 such that a plurality of staples can be deployed from the staple cavities 112.

In order to guarantee that the openings 117 of the staple cavities 112 on the staple cartridge 10 are aligned with the staple forming pockets 202 on the anvil 20 when the end effector clamps tissue to be stapled, the staple cartridge 10 is further provided thereon with a retaining pin assembly 102. The retaining pin assembly 102 is disposed in an end of the cartridge body 101 of the staple cartridge 10 proximate to the outside and operably connected to a closure drive mechanism 40 of the surgical stapler so as to extend distally out of a retaining pin hole 114 of a hollow cavity 113 opened on the tissue contact platform 111. In a preferred embodiment, a retaining pin assembly 102 is arranged perpendicular to the tissue contact platform 111 of the staple cartridge 10.

However, in the open surgical stapler according to the prior art, the retaining pin is typically centered relative to the longitudinal centerline of the staple cartridge while the staple holes are arranged symmetrically at two sides of the longitudinal centerline of the staple cartridge, as shown in FIG. 1. In other words, a longitudinal centerline of a plurality of rows of staple cavities 112 and the center of the retaining pin hole are located in the same straight line. In such arrangement, since the staple line formed by the outermost staple cannot cover the area where the retaining pin hole is located, a clearance is formed therebetween, where no staples are applied. In particular, when the area of the tissue to be stapled has a great width, the width of the tissue to be stapled often exceeds the respective lengths of the staple cartridge and the anvil of the stapler. In the circumstance, the retaining pin probably squeezes or even penetrates through the tissue when the tissue is clamped. At this time, the tissue around the retaining pin cannot be covered or stapled by the staples, causing a notch formed around the area where the retaining pin penetrates after stapling is completed, which probably results in local bleeding and tissue fluid leakage.

FIG. 3 illustrates a surface arrangement and structure of an improved staple cartridge of the surgical stapler according to the present disclosure. As shown therein, the tissue contact platform 111 of the staple cartridge 10 facing the anvil 20 is provided thereon with a plurality of rows of openings 117 of the staple cavities 112 allowing the staples to pass therethrough. The staple cavities 112 are arranged in two rows along the longitudinal direction L of the staple cartridge 10, which may also be arranged in three or more rows. At an end of the staple cartridge 10 proximate to the outside, the retaining pin assembly 102 is received in the hollow cavity 113 and configured to extend out of the retaining pin hole 114 formed on the tissue contact platform 111 and finally be inserted into a retaining pin receiving hole 203 formed on the anvil 20. As shown therein, the vertical direction L of the staple cartridge 10 and the vertical direction F of the stapler are generally perpendicular to each other.

In addition, as shown in FIG. 3, the retaining pin assembly 102 is arranged perpendicular to the tissue contact platform 111 of the staple cartridge 10. The retaining pin assembly 102 is slidable within the hollow cavity 113 along the longitudinal direction F of the stapler 1 (i.e., the retaining pin assembly 102 can slide from a mounting position fully received in the hollow cavity 102 to an end position extending into the retaining pin receiving hole 203 on the anvil 20) and operably coupled to the closure drive mechanism 40 of the surgical stapler 1. In this way, when the closure drive mechanism 40 is actuated, a pin rod 121 of the retaining pin assembly 102 extends distally out of the retaining pin hole 114 opened on the tissue contact platform 111 along the longitudinal direction F of the surgical stapler 1.

According to a preferred embodiment of the present disclosure, the retaining pin assembly 102 includes a pin rod 121 extending along the longitudinal direction of the retaining pin assembly 102. The pin rod 121 has a complete circular cross-sectional shape, and includes a free end 126 that can extend out of the retaining pin hole 114 and the other end opposing the free end. In the example, as compared with the existing design, the pin rod 121 is offset to one side relative to the centerline of the staple cartridge 10, causing the pin rod to maintain the complete circular cross-sectional shape and enabling the pin rod 102 to have a greater diameter. In an example, the pin rod of the retaining pin assembly has a diameter greater than 1.7 mm. Therefore, the solution can provide the pin rod with a greater strength, obviously improve the stability of the retaining pin assembly 102 during operation, and ensure that the pin rod 121 can smoothly enter the retaining pin receiving hole at the anvil side after penetrating the tissue, thereby guaranteeing a good staple forming effect.

FIG. 3 further shows a staple driver plate 103 arranged in the staple cartridge 10. The staple driver plate 103 extends along the longitudinal direction L of the staple cartridge 10 and is provided, on the surface of the distal end facing the surgical stapler 1, with a plurality of teeth extending towards the distal end of the surgical stapler 1, where the teeth are configured to push the staples out of the staple cavity 112. The staple driver plate 103 is operatively coupled to the firing drive mechanism (e.g., a firing bar 401) of the surgical stapler 1. In the case, the staple driver plate 103 is driven by the firing drive mechanism to move towards the distal end of the surgical stapler 1 when the firing trigger is pulled to perform a firing operation, and the plurality of teeth arranged thereon can push the staples to complete deployment accordingly.

Figure 4:
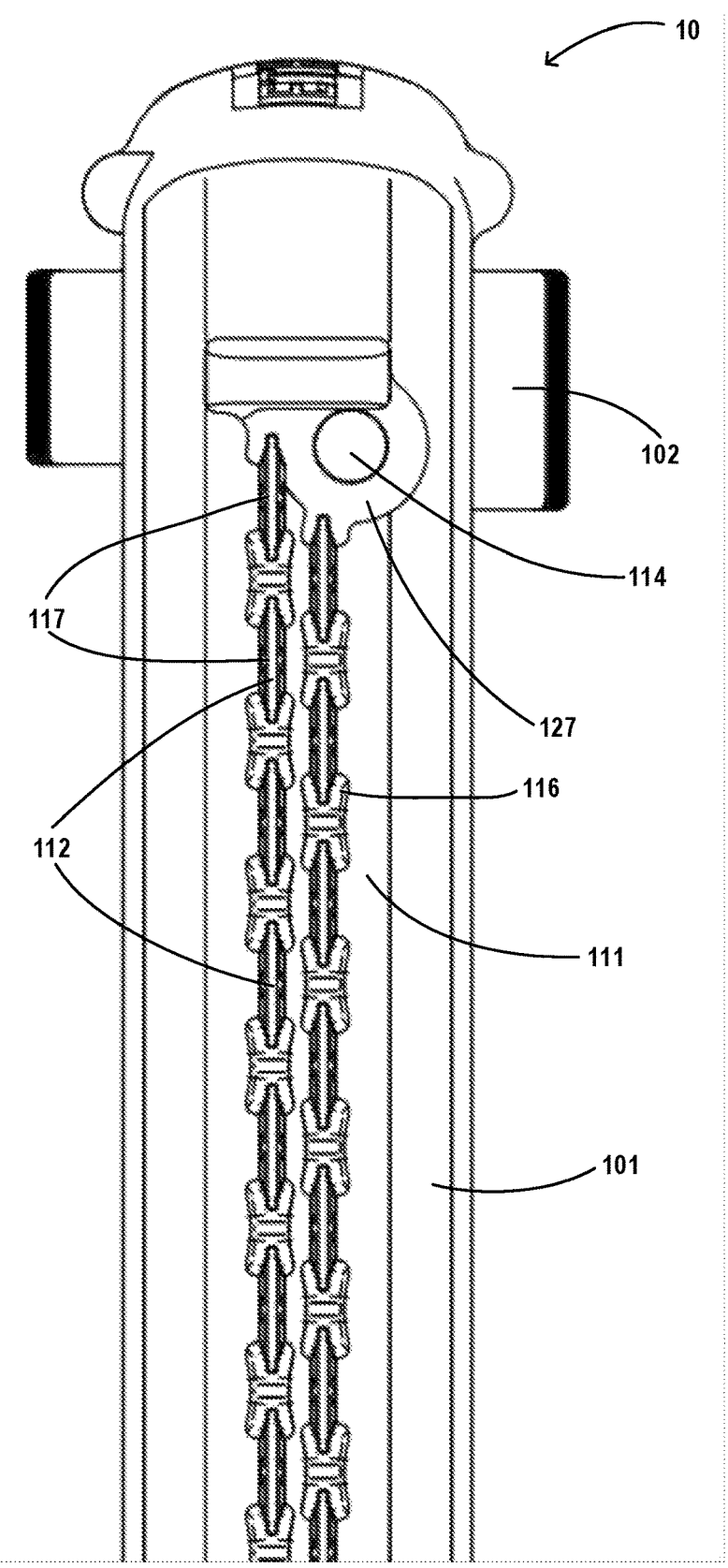
FIG. 4 is a main view of a staple cartridge according to the present disclosure.

FIG. 4 is a main view of the staple cartridge 10 according to the present disclosure. FIG. 4 clearly demonstrates the tissue contact platform 111 on the cartridge body 101 of the staple cartridge 10. The tissue contact platform 111 is provided thereon with two or more rows of staple cavities (the staple cavities 112 are arranged in two rows in the embodiment as shown in FIG. 4, which may be arranged in three or more rows in other embodiments) arranged in the longitudinal direction L of the staple cartridge 10 and a retaining pin hole 114 allowing the pin rod 121 of the retaining pin assembly 102 to extend therefrom. In the implementation as shown in FIG. 4, the two rows of staple cavities 112 are arranged in two sides of the longitudinal centerline of the staple cartridge along the longitudinal direction L of the staple cartridge 10, where the longitudinal centerline thereof coincides with the longitudinal centerline of the staple cartridge, and the retaining pin hole 114 for receiving the retaining pin assembly 112 is offset relative to the centerline of the staple cartridge 10 such that the outermost edge of the outermost staple cavity in a row of the staple cavities 112 is aligned with or extends from the center of the pin rod 121 of the retaining pin or the center of the retaining pin hole 114. With such arrangement, the present disclosure can accomplish that the staple line located at the outermost side after firing at least covers a half of the retaining pin hole 114, thereby ensuring the tissue stapling effect and reducing the risks of bleeding and tissue fluid leakage.

According to a preferred implementation of the present disclosure, the pin rod 121 of the retaining pin assembly 102 is offset relative to the longitudinal centerline of the staple cartridge 10, and the longitudinal centerline of the plurality of rows of the staple cavities 112 is offset relative to the longitudinal centerline of the staple cartridge 10. Alternatively, according to a further solution, the pin rod 121 of the retaining pin assembly 102 is centered relative to the longitudinal centerline of the staple cartridge 10, and the longitudinal centerline of the plurality of rows of the staple cavities 112 is offset relative to the longitudinal centerline of the staple cartridge 10.

In an example according to the present disclosure, the staple cavities 112 are arranged in two rows, where the two rows of the staple cavities 112 may have the same length, or different length. In an event that the two rows of the staple cavities have different lengths, the outermost edge of the outermost staple cavity in the relatively longer staple cavity row extends beyond the longitudinal axis of the pin rod 121 while the relatively shorter staple cavity row is adjacent to an opening 114 of a chute 113. In an event that the two rows of the staple cavities have the same lengths, the two rows of the staple cavities are arranged offset, wherein the outermost edge of the outermost staple cavity in one row of staple cavities extends beyond the longitudinal axis of the pin rod 121, while the outermost edge of the outermost staple cavity in another row of staple cavities is adjacent to an opening 114 of a chute 113. In this way, the blood or fluid leakage can be further reduced.

In addition, as shown in FIG. 4, the cartridge body 101 further includes a plurality of ridges 116 extending from the tissue contact platform 111 towards the distal end of the surgical stapler 1, where two adjacent ends of the two adjacent staple cavity opening 117 is surrounded by a respective ridge 116. Alternatively, at least a part of each staple cavity opening 117 is surrounded by a portion of a respective ridge 116 or portions of ridges. As such, when the jaws are closed, the ridges 116 first contact the tissue, to prevent or at least restrict a relative movement between the tissue and the staple cartridge.

Moreover, a ring-like bump 127 may be formed around the retaining pin hole 114. Alternatively, the bump 127 only surround a part of the retaining pin hole 114. The bump cannot only provide better guidance and extra support to the pin rod 121 when the retaining pin assembly is actuated, but also can prevent the tissue from be squeezed out of the end effector when the end effector is closed.

FIG. 5 is a perspective view illustrating a part of an end effector 1 according to the present disclosure. The section shown in FIG. 5 is a section of the end effector having a jaw structure and located adjacent to the outside. It can be seen that the anvil 20 includes a tissue contact surface 201, and the tissue contact surface of the anvil 20 is configured thereon with a plurality of staple forming pockets 202 for stapling-deforming the staples, which are arranged in rows corresponding to the plurality of staple cavities 112 on the staple cartridge.

In addition, the tissue contact surface 201 of the anvil 20 is further provided with a retaining pin receiving hole 201 for receiving and locating the pin rod of the retaining pin assembly 102. The retaining pin receiving hole 203 is aligned with a retaining pin chute opening 114 on the cartridge body 101 of the staple cartridge 10 such that the staple cavity openings 117 of the staple cavities 112 on the staple cartridge 10 are aligned with the staple forming pockets 202 on the anvil 20 when the end effector 1 is clamping tissue to be stapled. When the jaws of the end effector are closed to clamp tissue, the pin rod of the retaining pin assembly 102 of the staple cartridge 10 can extend out of the retaining pin chute opening 114 as the retaining pin assembly 102 is sliding within the retaining pin chute 113, and a free end 126 of the pin rod 121 can be inserted into the retaining pin receiving hole 203.

As shown in FIG. 5, similar to the situation of the staple cavity 112 and the retaining pin chute opening 114 on the staple cartridge, the outermost edge of the outermost staple forming pocket in the at least one row of the staple forming pockets 202 is aligned with or extends out of the center of the retaining pin hole in the longitudinal direction L of the anvil 20, such that the retaining pin receiving hole 203 and the staple forming pockets 202 on the anvil 20 are aligned with the retaining pin chute opening 114 and the staple cavities 112 in the embodiment as shown in FIG. 4, respectively. In the embodiment as shown in FIG. 5, the retaining pin receiving hole 203 is configured with a cylindrical shape, and the respective retaining pin chute opening 114 is correspondingly configured with a round shape. Of course, other shapes of the retaining receiving hole 203 and the retaining pin chute opening 114 conceivable to those skilled in the art can be adopted as long as the retaining pin assembly 102 can be positioned, which all fall into the protection scope of the present disclosure.

Furthermore, as can be seen from FIG. 5, the cartridge body 101 of the staple cartridge 10 at two sides is further configured with a slot 115 extending along the longitudinal direction F of the surgical stapler 1 such that a respective structure of the retaining pin assembly 102 extends out of the cartridge body 101 in the preferred embodiment.

Figure 6A:
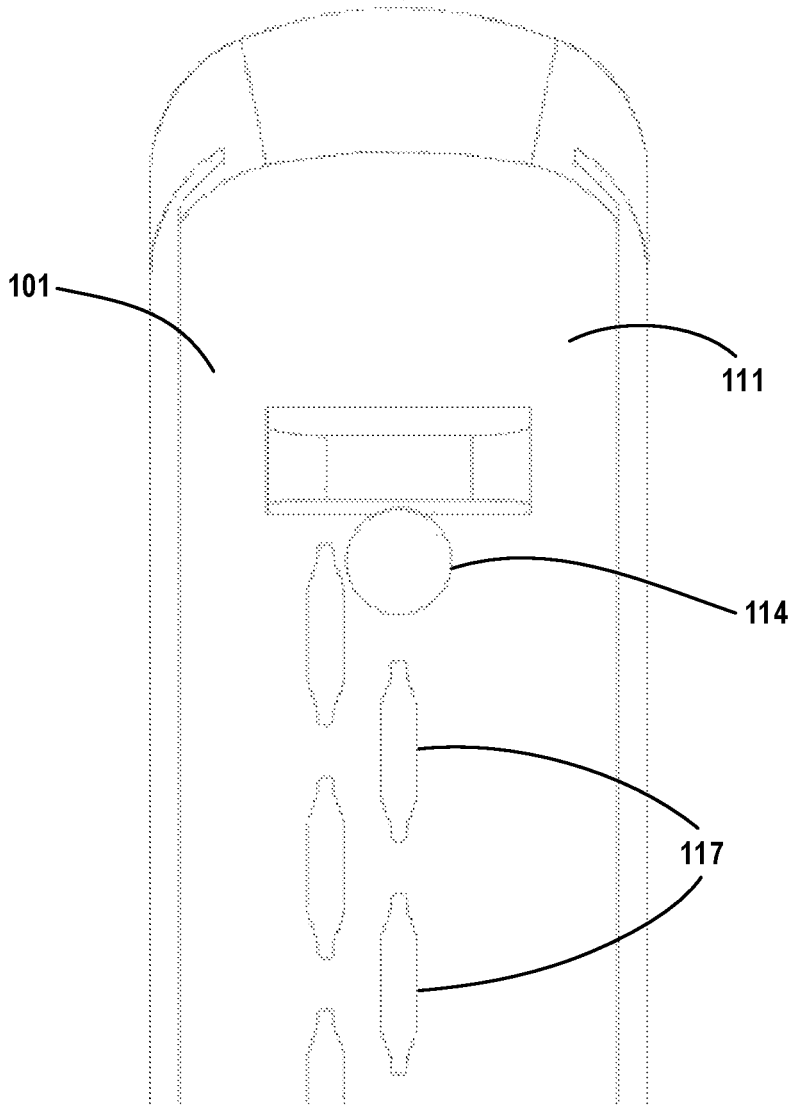
FIGS. 6a and 6b are schematic views respectively illustrating a part of a staple cartridge according to different preferred implementations of the present disclosure.
Figure 6B:
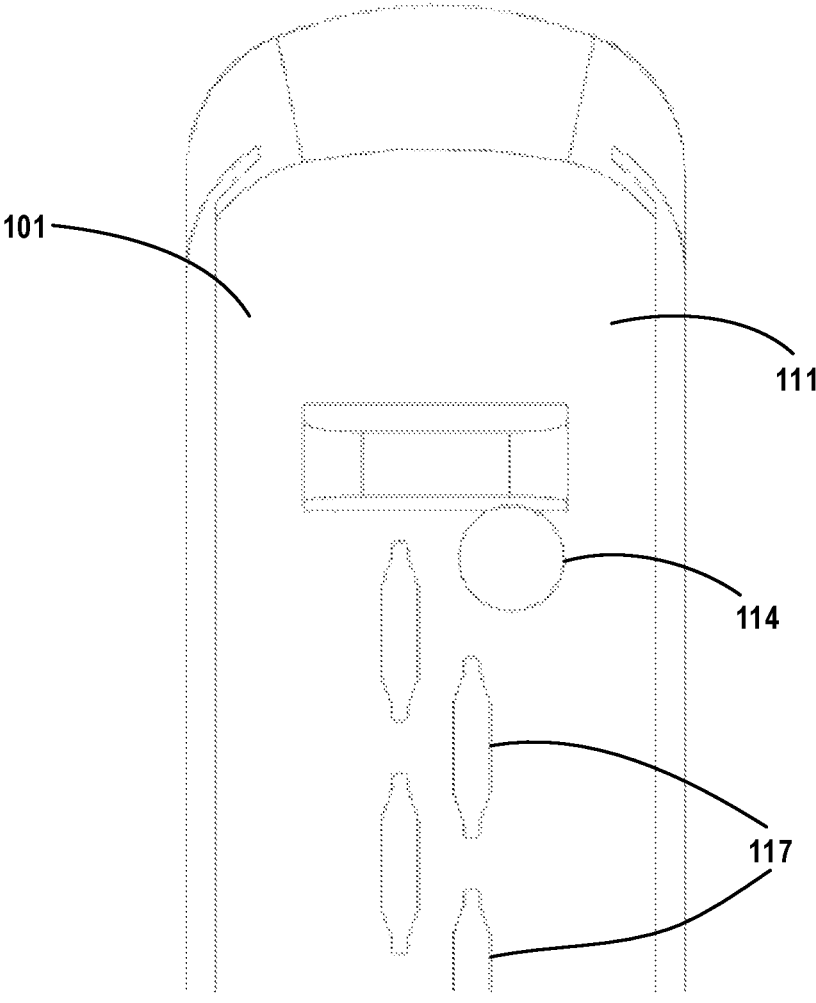

As described above, in the embodiment of the staple cartridge 10 as shown in FIG. 4, the retaining pin assembly 102 is offset relative to the longitudinal centerline of the staple cartridge 10 while the longitudinal centerline of the plurality of rows of the staple cavities 112 coincides with the longitudinal centerline of the staple cartridge 10. Therefore, as observed from the main view of the staple cartridge 10, the staple cavity openings 117 are wholly centered on the tissue contact platform 111 while the retaining pin hole 114 is arranged offset. By contrast, FIGS. 6a and 6b illustrate another two possible preferred embodiments of the staple cartridge 10, respectively. Wherein, in the embodiment as shown in FIG. 6a, the pin rod 121 of the retaining pin assembly 102 is centered relative to the longitudinal centerline of the staple cartridge 10 while the longitudinal centerline of the plurality of rows of the staple cavities 112 are offset relative to the longitudinal centerline of the staple cartridge 10. In the case, the staple cavity openings 117 are offset as a whole on the tissue contact platform 111 while the retaining pin hole 114 is centered. In the embodiment as shown in FIG. 6b, the retaining rod 1121 of the retaining pin assembly 102 is offset relative to the longitudinal centerline of the staple cartridge 10 while the longitudinal centerline of the plurality of rows of the staple cavities 112 are offset relative to the longitudinal centerline of the staple cartridge. In the case, the retaining pin hole 114 and the staple cavity openings 117 are all offset on the tissue contact platform 111.

Figure 7A:
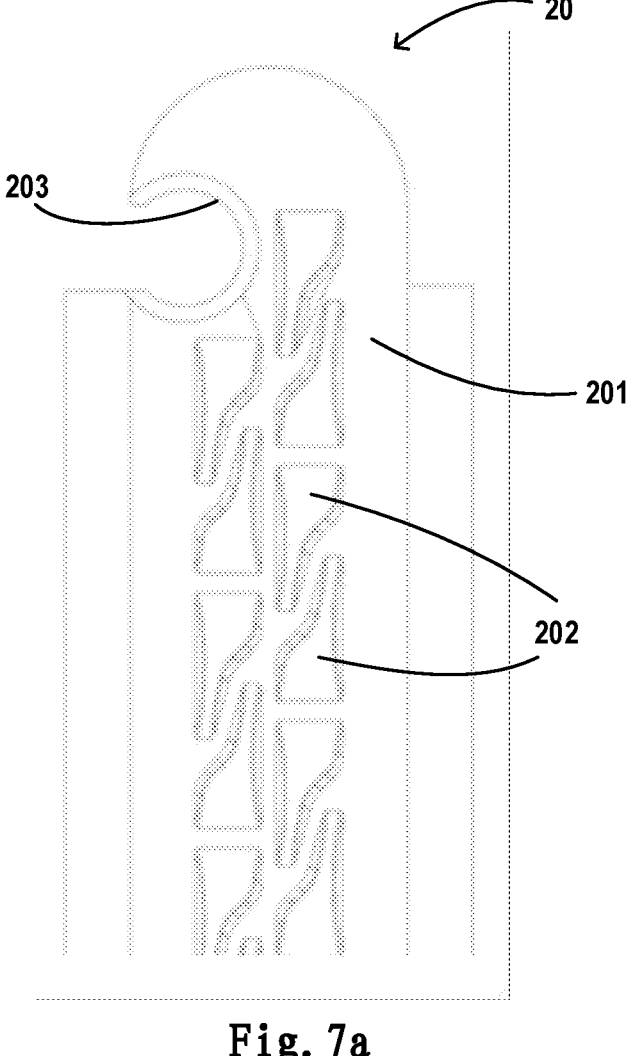
FIGS. 7a and 7b are schematic views respectively illustrating a part of an anvil in different preferred implementations of the surgical stapler according to the present disclosure.
Figure 7B:
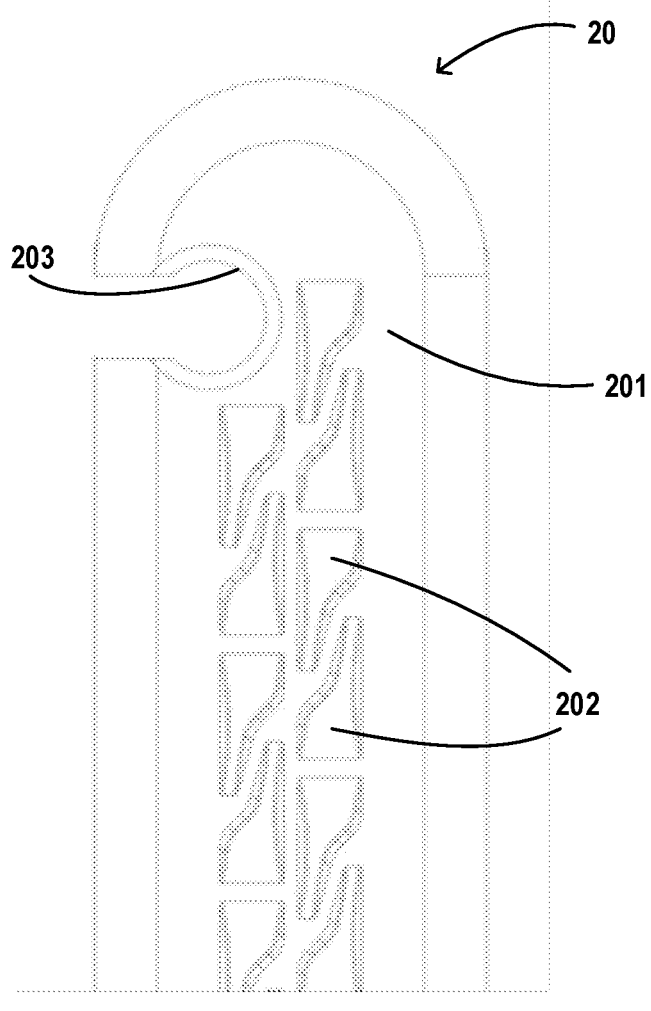

FIGS. 7a and 7b are schematic views of a part of an anvil according to different preferred implementations of the surgical stapler of the present disclosure. As shown in FIG. 7a, the retaining pin receiving hole 203 on the anvil 20 is configured to open towards the side surface of the anvil along the transverse direction of the anvil 20. As shown in FIG. 7b, the retaining pin receiving hole 203 on the anvil 20 connects to the outside via a notch formed on an edge of the anvil at one side proximate to the retaining pin receiving hole. In the embodiments as shown in FIGS. 7a and 7b, the retaining pin receiving hole 203 has an incomplete circular shape, preferably an eccentric semicircle, for example. The retaining pin receiving hole 203 having such shape can also receive a tip-like free end 126 of the retaining pin assembly 102, thereby fulfilling the positioning function of the retaining pin assembly 102.

Figure 8A:
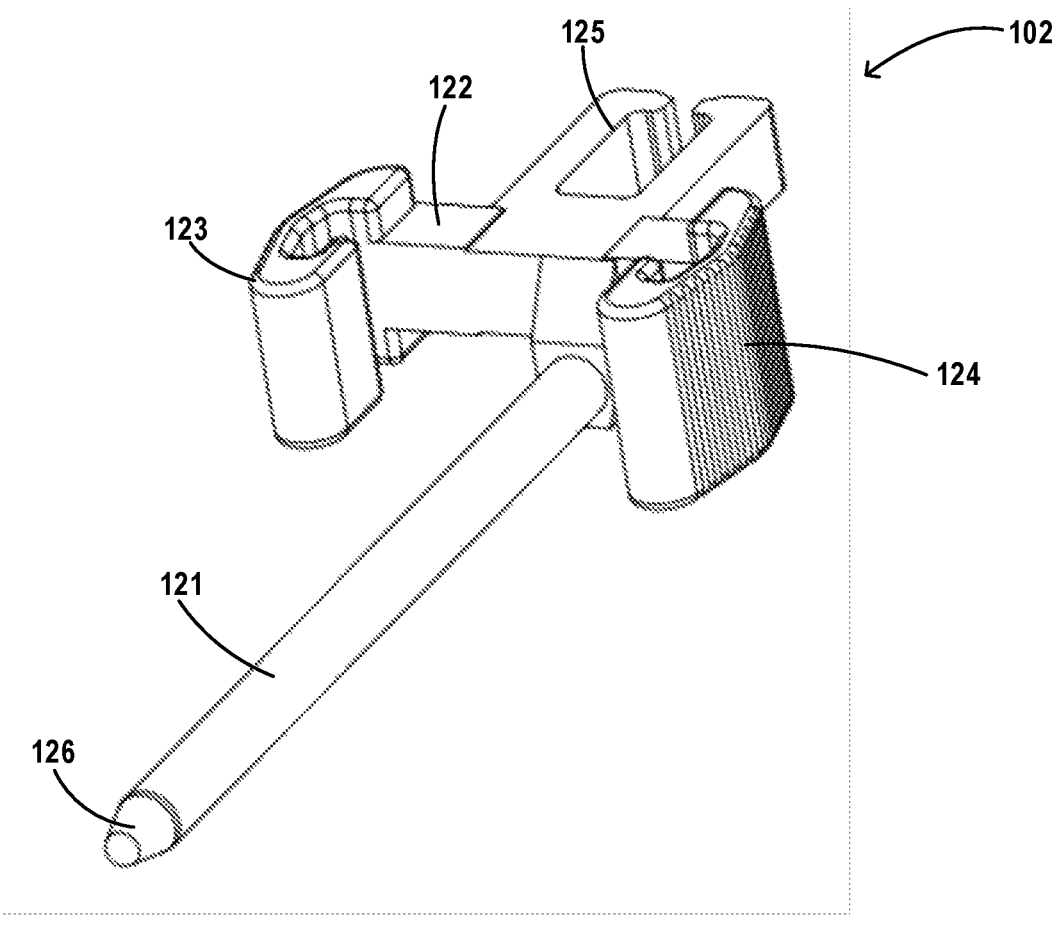
FIGS. 8a through 8c are respectively a perspective view, side view and bottom view of a retaining pin hole according to the present disclosure.
Figure 8B:
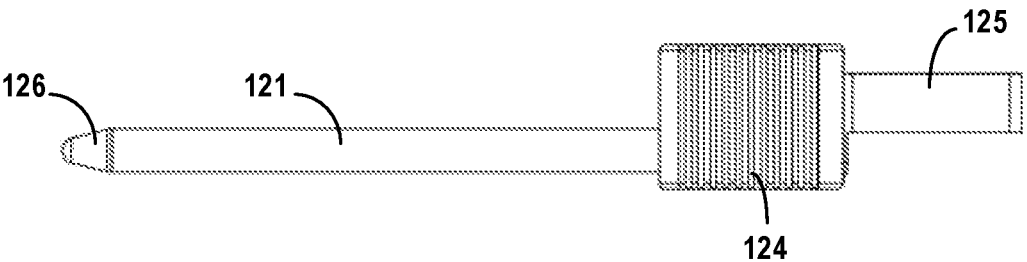
Figure 8C:
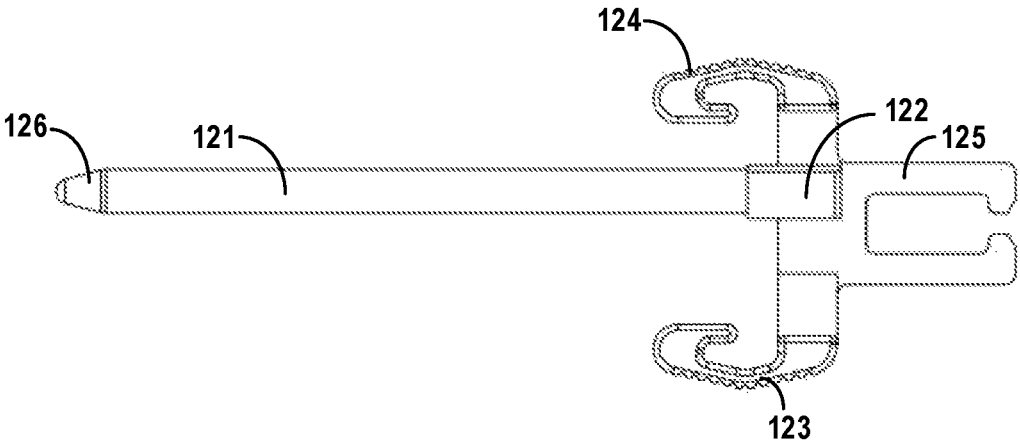

FIG. 8 schematically illustrates a structure of a retaining pin assembly 102 of a staple cartridge 10 according to a preferred embodiment of the present disclosure from multiple perspectives, where FIGS. 8a through 8c are a perspective view, a side view and a bottom view of the retaining pin assembly 102, respectively.

As shown in FIGS. 8a through 8c, the retaining pin assembly 102 includes: a pin rod 121 extending along its longitudinal direction, which includes a tip-like free end 126 that can extend out of the retaining pin hole 114 of the cartridge body 101, and the other end opposing the free end; a pin base 122 connected to the other end of the pin rod 121 to fixedly retain the pin rod 121; and a retaining pin tail 125 that is fixed on a side of the pin base 122 away from the pin rod 122 in the embodiment, and formed with two legs spaced apart from each other.

In addition, as shown in FIG. 8a, the retaining pin assembly 102 further includes a pair of clips 123, 124 disposed at two sides of the pin base 122. The pair of clips 123 and 124 are configured thereon with a wrinkled or corrugated structure for the anti-slip purpose when they are held by a clinician. When the closure drive mechanism 40 is not actuated, the clinician can operate the clips 123, 124 with fingers to manually cause the retaining pin assembly 102 to slide within the retaining pin chute 113. The clips 123, 124 are configured on the two side surfaces of the cartridge body 101 and extend out of the cartridge body 101 along the slots 115 extending in the longitudinal direction of the stapler, as shown in FIG. 5, such that the retaining pin assembly 102 is operated by the user to slide along the retaining pin chute 113. According to a preferred implementation, as shown in FIGS. 8a and 8c, the clips 123, 124 have an ear-like structure.

Figure 9A:
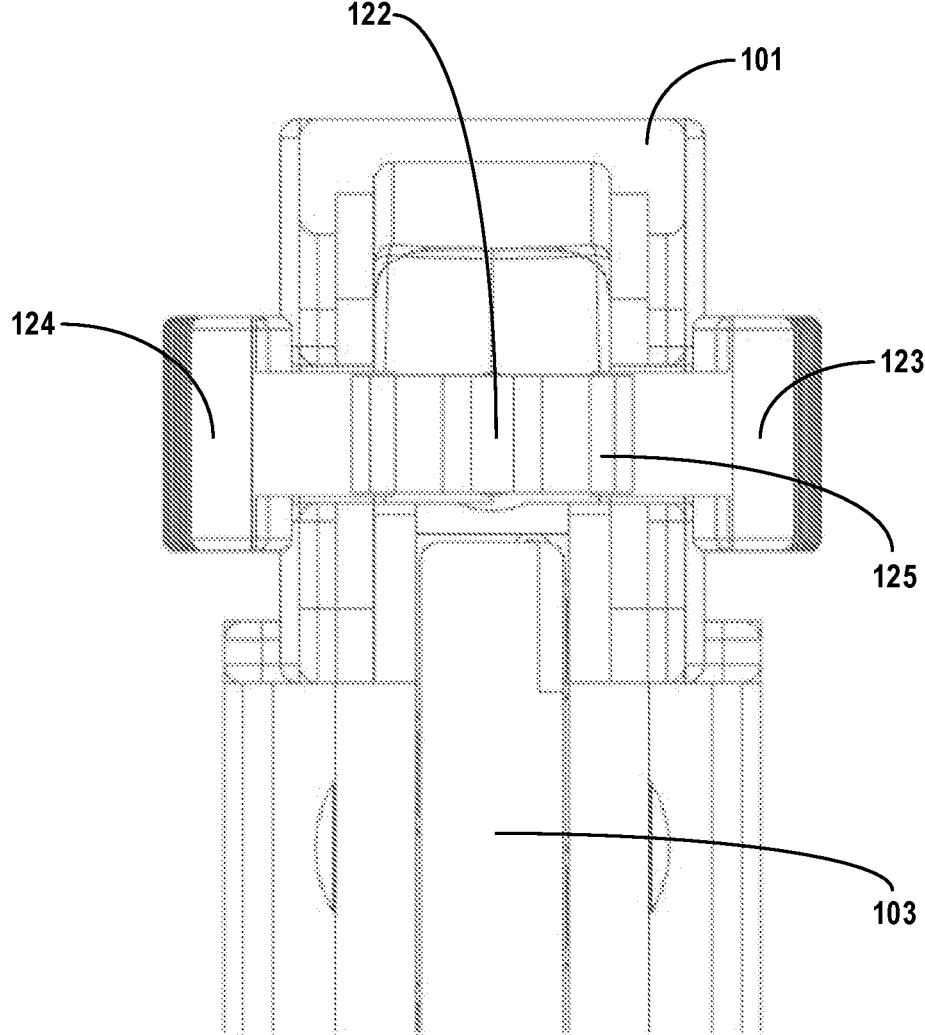
FIGS. 9a and 9b are rear views of an end effector, illustrating structures of a retaining pin assembly and a staple driving panel and a relation therebetween, where
Figure 9B:
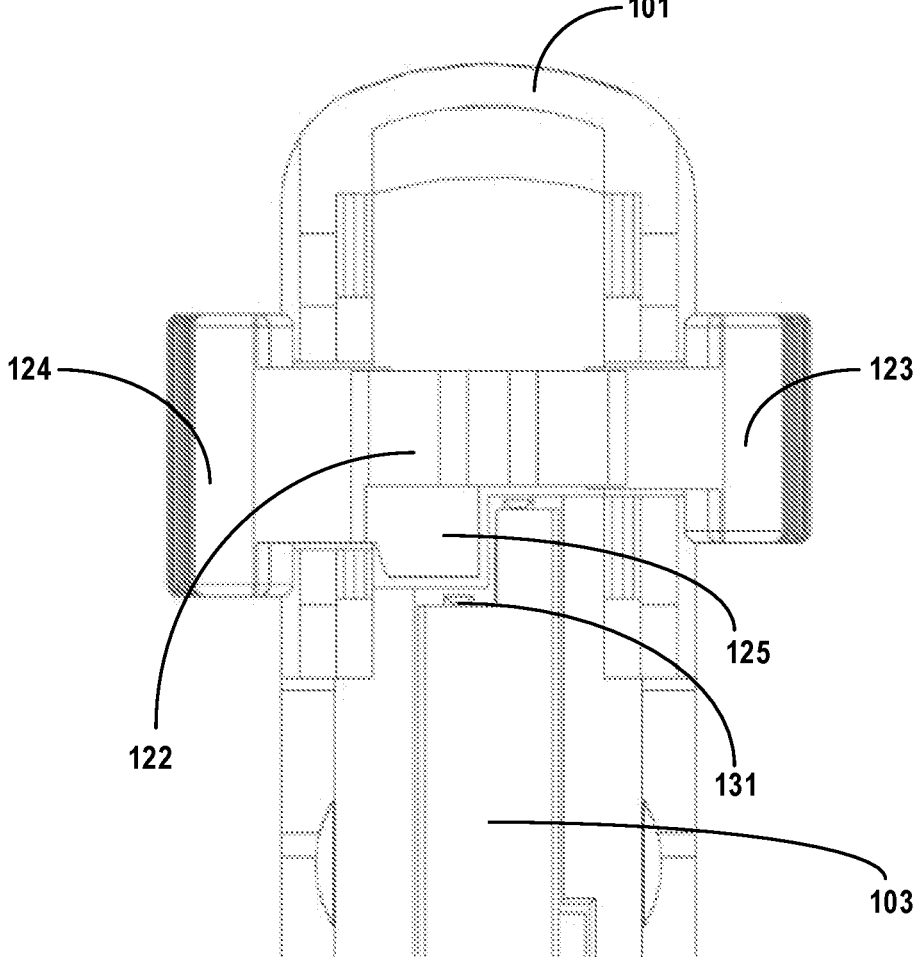

FIG. 9 is a rear view of the end effector, illustrating structures of a retaining pin assembly 102 and a staple driver plate 103 of the staple cartridge 10 and a relative relation therebetween, where the FIG. 9a is a view according to the prior art, and FIG. 9b is a view according to a preferred embodiment of the present disclosure.

In the prior art, the pin rod 121 of the retaining pin assembly 102 is generally centered relative to the pin base 122. As shown in FIG. 9a, a pair of clips 123, 124 are configured mirror-symmetrically about the central axis of the retaining pin assembly, the retaining pin assembly 102 is entirely located above the staple driver plate 103, and the pin base 122 can pass above an edge surface of the staple driver plate 103.

FIGS. 8a through 8c illustrate a retaining pin assembly according to preferred embodiments of the present disclosure, respectively. In particular, the pin rod 121 of the retaining pin assembly 102 is offset relative to the longitudinal center axis of the pin base 122. In order to reinforce the entire strength of the retaining pin assembly 102 when the pin rod 121 is offset, the pin rod 121 offset is designed to have asymmetric structures at two sides. For example, according to a preferred implementation, at one side where the pin rod 121 offset has a small distance from the transverse edge of the pin base 122 (namely the side towards which the pin rod 121 is offset), the pin base 122 is increased in thickness. Furthermore, in order to adapt to the offset design of the pin rod 121 and prevent the retaining pin assembly 102 from inclining or pivoting caused by an uneven stress distribution when the clips 123, 124 are manually pushed, the pair of clams 123, 124 are also designed not to be mirror-symmetrical around the central axis of the retaining pin assembly 102, i.e., the clip 124 located at the side to which the pin rod 121 is offset is configured to be larger than the clip 123 at the side from which the pin rod 121 is offset. In other words, the ear-like clips 123, 124 at two sides of the pin base are of different dimensions.

However, the disadvantage to the retaining pin assembly as shown in FIGS. 8a through 8c lies in that, since the pin rod 121 is offset and the pin base 122 at the side to which the pin rod 121 is offset is increased in thickness, a part of the pin base 122 probably interferes with the staple driver plate 103 in the longitudinal direction L of the staple cartridge, making it impossible to manually push the retaining pin assembly 102 over the staple driver plate 103.

Figure 10:
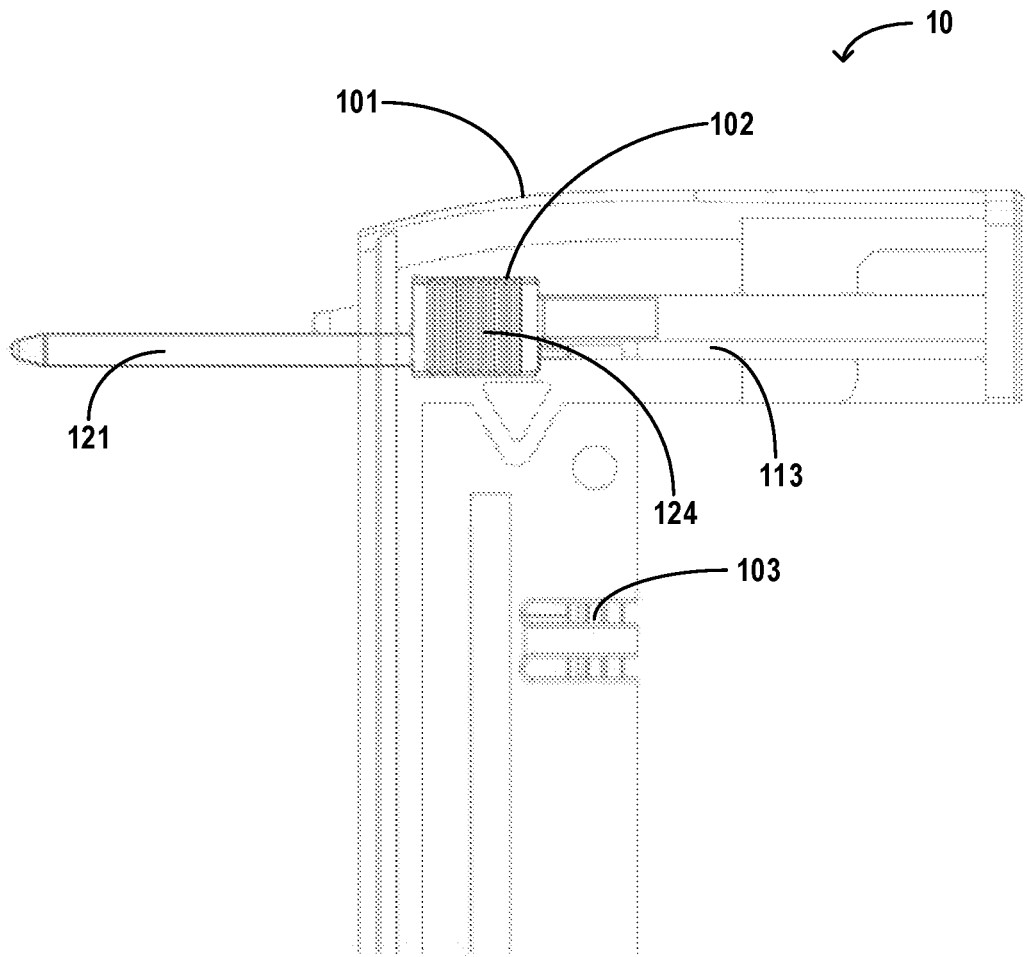
FIG. 10 is a view of pushing the retaining pin assembly as shown in FIG. 9b distally past the staple driver plate to its end position.

In order to solve the above problem, a possible solution is to increase the length of the pin rod 121 to cause the free end 126 of the pin rod 121 to arrive at the retaining pin receiving hole 203 on the anvil 20 before the pin base 122 interferes with the staple driver plate 103. However, the retaining pin assembly 102 will have a great overall length, and the cartridge body 101 will accordingly have a great length along the longitudinal direction F of the stapler, thus making a compact structure impossible. To this end, FIG. 9b illustrates an embodiment adapted to the retaining pin assembly 102 as shown in FIG. 8, which can avoid interference between the retaining pin assembly 102 and the staple driver plate 103 in the premise of guaranteeing the offset structure of the retaining pin assembly 102 and the overall compact structure of the staple cartridge. In the embodiment, the staple driver plate 103 at its distal end portion adjacent to the retaining pin assembly 102 is formed with an avoidance feature 131, for example, a cutout formed at the distal end portion of the staple driver plate adjacent to the retaining pin assembly. The cutout extends along the longitudinal direction F of the stapler and is configured to avoid the retaining pin assembly 102, in particular to allow the pin base 122 of the retaining pin assembly to pass therethrough. In this way, the retaining pin assembly 102 can advance towards the distal end of the surgical stapler 1 and fully pass through the staple driver plate 103, as shown in FIG. 10. According to the embodiment, the retaining pin assembly 102 can be pushed distally until reaching the end position.

In addition to the end effector located at the distal end of the stapler, the surgical stapler further includes a closure and fire mechanism located at the proximal end of the stapler for closing the staple cartridge and the anvil to clamp tissue to be stapled, and implementing a severing and stapling operation on the tissue. The closure and fire mechanism generally includes a pistol grip connected to a handle 70 of the surgical stapler, a closure trigger pivotally fixed on the handle 70 of the surgical stapler and coupled to a drive mechanism of the staple cartridge or anvil, and a firing trigger pivotally fixed on the handle 70 and coupled to the drive mechanism of the staple.

During surgery, a clinician can grip the pistol grip and then pivotally pull the closure trigger. In the case, the closure trigger actuates the closure drive mechanism of the staple cartridge and thus causes the staple cartridge to move relative to the anvil, so as to close the end effector and clamp the tissue. The firing trigger is disposed at one side away from the pistol grip with respect to the closure trigger and can be pivotably pulled by the clinician, thereby causing actuation of the firing drive mechanism of the stapler and further driving the staple driver plate to push staples towards the tissue to staple the latter.

In practice, after gripping the grip, a user first actuates the closure trigger, manipulates the retaining pin assembly for positioning when satisfied with the relative positions of the staple cartridge and the anvil of the end effector, and then fixes the closure trigger at the fully closed, locked position to clamp the tissue. Thereafter, the user actuates the firing trigger to actuate the firing bar 401 to move towards the end effector, and further cause the staple driver plate to move towards the tissue to implement stapling. During the process, the user needs to continuously apply a force to the firing trigger to fire the staples towards the tissue. After the stapling is completed, the user stops applying the force, and the firing trigger is restored. When, for example, a release button 504 on the handle 70 is pressed, the locking of the closure trigger is released, and the retaining pin assembly is released accordingly to finally release the stapled tissue. In the case of tissue to be stapled having a great length, the process needs to be iterated until all tissue is stapled.

It would be appreciated that the traditional surgical stapler often relies on the user experience to determine whether the staples are in situ and whether the stapling is completed, so as to determine whether to stop applying the force. However, this poses a great change to a common user and is not conductive to standardizing surgical operations. Furthermore, the traditional surgical stapler may a single firing operation time prolonged and reduce the operation efficiency, thus bringing certain risks to the operation and the patient.

In view of the above, there is further provided an indication mechanism perceptibly indicating a user that a firing operation has been completed according to the present disclosure. By means of the indication mechanism, a user manipulating the surgical stapler can be perceptibly indicated that a firing operation has been completed, making it possible to complete the stapling in time, or reset the end effector and the closure and fire mechanism and then continue to iterate the operation as described above to perform a further firing operation.

According to a first implementation of the indication mechanism, the indication can be implemented visually. More specifically, a mark is provided at a specific location on the upper surface of the firing bar 401 of the firing drive mechanism coupled to the firing trigger. The mark can be arranged in a spacer at the left side and/or the right side of the firing bar 401, and the spacers at the left and right sides are assembled on the firing bar 401 and move along with the latter. The mark may be a circle, square or any other shape or pattern visually noticeable. The mark may be a laser mark, engraved mark, ink mark or the like. Accompanied with the actuation of the firing trigger, the mark may be moved along with the firing bar towards the end effector. The mark is hidden in a shroud 505 of the stapler until a complete firing operation has been completed, and upon the completion of the firing operation, the mark is just entirely exposed from the shroud 505 of the stapler so as to be spotted by the user visually, thus prompting the user that the firing operation has been completed.

In addition, according to a second implementation of the indication mechanism, an indication can be achieved audibly and/or tactilely. More specifically, a protrusion is disposed at the rear side of the firing trigger of the closure and fire mechanism away from the end effector, and a button that makes a sound upon being pressed is disposed at the front side of the closure trigger facing the end effector. For example, the button is made of rubber. Of course, a technical solution where a button is disposed at the rear side of the firing trigger and a protrusion is disposed at the front side of the firing trigger is allowed. The protrusion and the button are designed such that when the firing trigger is pivoted to a firing completion position, the protrusion can fully depress the button, making the latter to produce a click sound or the like and thus prompt the user that a firing operation has been completed. Moreover, the button, for example, can be configured to provide a force feedback when fully depressed by the protrusion, to enable a user to tactilely sense with a finger an indication that a firing operation has been completed.

In addition to the two types of indication mechanisms that can give an indication that a firing operation has been completed, as described above, there may be other technical solutions that can enable a user to perceptibly (e.g., in an audible, visual, or tactile fashion) realize that a firing operation of the surgical stapler has been completed, which also fall into the scope as disclosed herein.

Figure 11A:
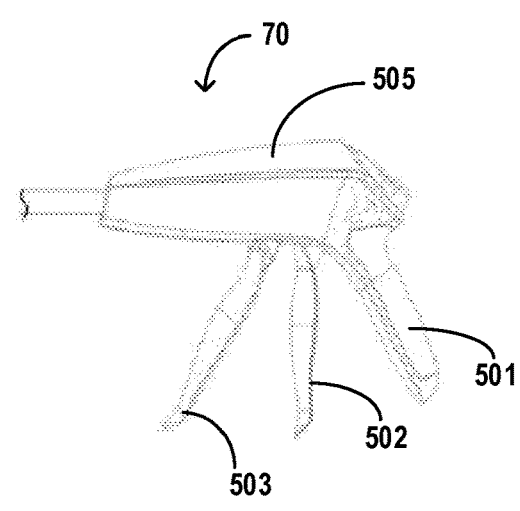
FIGS. 11a through 11c are schematic views respectively illustrating a closure trigger and a firing trigger of a closure and fire mechanism of a surgical stapler according to the present disclosure.
Figure 11B:
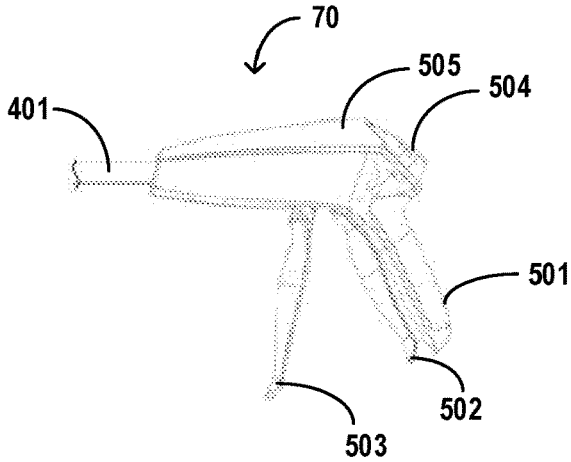
Figure 11C:
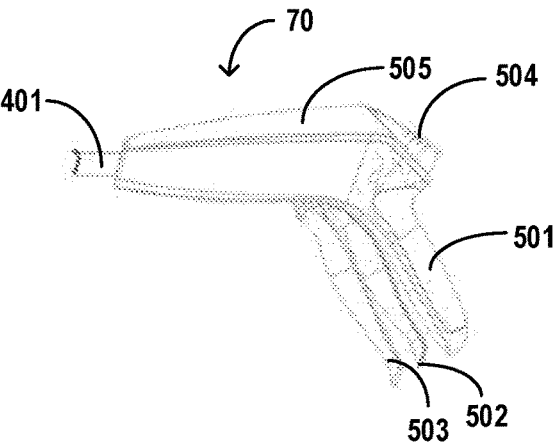

FIGS. 11a through 11c are schematic views illustrating relative positions of a closure trigger 502 and a firing trigger 503 of a closure and firing mechanism according to the present disclosure in different states, where only a truncated section of the closure and fire mechanism of the surgical stapler is shown. The closure and fire mechanism can be fit with various types of end effectors 1 and thus can be applied to open surgery or endoscopic surgery as required specifically.

As shown in FIG. 11a, the closure and fire mechanism is disposed within a main body frame 30 of the surgical stapler. The closure and fire mechanism includes a piston grip 501 fixedly connected to the main body frame 30, and a closure trigger 502 and a firing trigger 503 pivotably configured with respect to the grip. The closure trigger 502 and the firing trigger 503 are coupled to the firing drive mechanism 40. The closure trigger 502 can push the staple cartridge 10 and the retaining pin assembly 102 via the firing drive mechanism 40 to move towards the anvil 20, thereby allowing the end effector 1 to enter a closed state, and the firing trigger 503 can further drive the staple driver plate 103 to drive respective staple drivers and finally push the staples to implement firing. When the end effector 1 of the surgical stapler is in a non-working state or open state, the firing trigger 503, closure trigger 502 and pistol grip 501 are spaced apart from one another.

As shown in FIG. 11b, after a surgical procedure is started, tissue to be stapled is first placed in a predetermined position relative to the end effector 1 of the surgical stapler, specifically between the anvil 20 and the staple cartridge 10. After position alignment is performed, a clinician manipulates the retaining pin assembly 102 to position the tissue to be stapled relative to the staple cartridge 10 and the anvil 20. Then, the clinician pulls the closure trigger 502 towards the grip 501. Then, the closure trigger 502 pivots counterclockwise and pushes the staple cartridge 10 and the retaining pin assembly 102 via the firing drive mechanism 40 to move towards the anvil 20, thereby clamping the tissue. After the tissue is fully clamped, the clinician can lock the closure trigger 502 relative to the grip by triggering a locking button (not shown), and the end effector 1 of the stapler is in a closed state at this time.

Further referring to FIG. 11c, after the tissue is positioned and clamped, the clinician may start stapling. The clinician pulls the firing trigger 503 towards the grip. Then, the firing trigger 503 actuates the staple driver plate 103 via a firing bar (not shown) to actuate the staples to be fired. In the firing process, the clinician needs to continuously apply a force to the firing trigger 503, and after the clinician determines that a firing operation has been completed, the firing trigger 503 is pivoted to a firing completion position adjacent to the closure trigger.

As aforementioned, in the firing process, it relies on the clinician's experience to determine whether the staples are in in situ and whether the stapling has been completed, so as to determine whether to stop applying the force. According to the present disclosure, there is provided an indication mechanism 60 enabling a clinician to perceptibly sense the indication that the firing operation has been completed.

Figure 12:
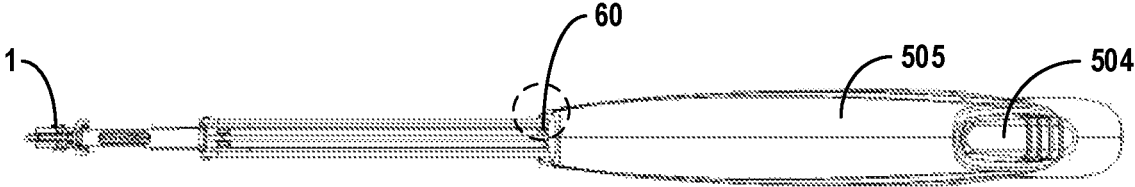
FIG. 12 is a schematic view illustrating an implementation of a closure and fire mechanism of a surgical stapler according to the present disclosure in a firing completion state.
Figure 13:
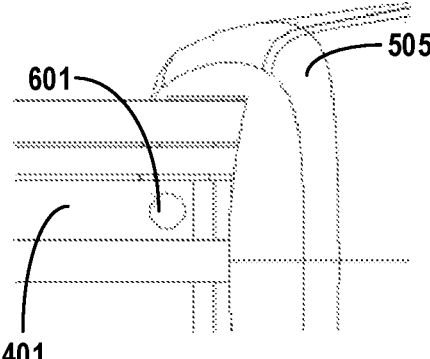
FIG. 13 is a partial enlarged view of an indication mechanism as shown in FIG. 12.

Reference now will be made to illustrate two feasible implementations of the indication mechanism 60. FIGS. 12 and 13 illustrate an implementation of the indication mechanism 60, where FIG. 12 is a top view of an implementation of a closure and fire mechanism of a surgical stapler according to the present disclosure in a firing completion state, and FIG. 13 is a partial enlarged view of the indication mechanism as shown in FIG. 12. Wherein, an indicator mark 601 is used to indicate that a firing operation has been completed. More specifically, an indicator mark 601 is provided at a specific location on the upper surface of the firing bar 401 coupled to the firing trigger 503. During firing, the indicator mark 601 moves along with the firing bar 401 relative to the shroud 505 of the pistol grip 501. In the implementation as shown in FIGS. 12 and 13, the mark 601 is a circle, which may also be a square or any other shape or pattern visually noticeable. Accompanied with actuation of the firing trigger 503, the mark 601 can move along with the firing bar 401 towards the end effector 1. The mark 601 is hidden in a shroud 505 of the pistol grip 501 until a complete firing operation has been completed, and upon completion of the firing operation, the mark 601 is just entirely exposed from the shroud 505 to be spotted by the user visually, thus prompting the user that the firing operation has been completed.

Figure 14:
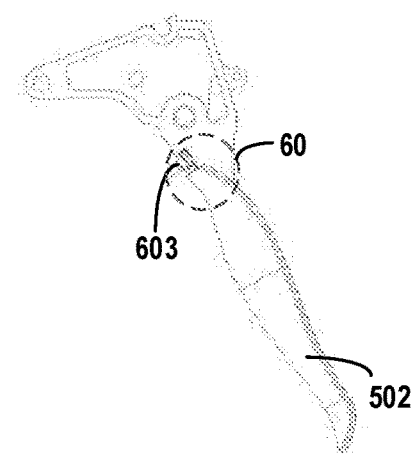
FIG. 14 is a schematic view illustrating a closure trigger in a further implementation of the closing and triggering mechanism of a surgical stapler according to the present disclosure.
Figure 15:
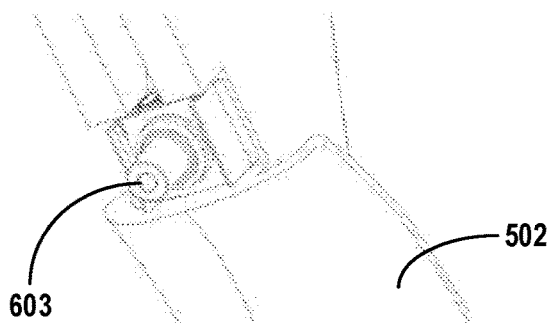
FIG. 15 is a partially enlarged perspective view of the closure trigger as shown in FIG. 14.
Figure 16:
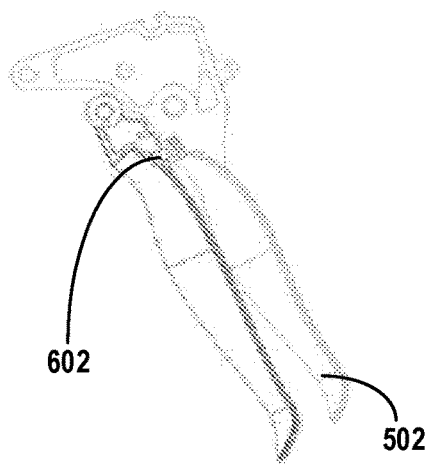
FIG. 16 is a schematic view of the closure and fire mechanism as shown in FIGS. 14 and 15 in a firing completion state.

FIGS. 14 through 16 illustrate a further implementation of the indication mechanism, where a sound is used to indicate that a firing operation has been completed. In the implementation, the indication can be implemented audibly and/or tactilely. The closing trigger 502 and the firing trigger 503 of the closure and fire mechanism include a pivot section and a trigger section, respectively. As shown in FIGS. 14 and 15, at a connection between the pivot section and the trigger section of the firing trigger 503, a protrusion 602 is disposed at one side of the firing trigger 503 away from the end effector 1, and at a connection between the pivot section and the trigger section of the closure trigger 502, a button 603 that makes a sound when depressed, in particular a rubber button, is disposed on a side of the closure trigger 502 facing the end effector 1. As shown in FIG. 16, the protrusion 602 and the button 603 are designed such that when the firing trigger is pivoted to a firing completion position, the button 603 can be fully depressed by the protrusion 602 to produce a click sound or the like, thus prompting the clinician that a firing operation has been completed. In addition, when a rubber button is utilized, for example, it may be preset that the button 603 can provide a force feedback when fully depressed by the protrusion 602, to enable the clinician to tactilely sense with a finger an indication that a firing operation has been completed.

FIG. 15 is a partially enlarged perspective view of the closure trigger as shown in FIG. 14, where a button 603, in particular a rubber button, at a connection between the pivot section and the trigger section of the closure trigger 502 is shown. FIG. 16 illustrates a position of the firing trigger 503 relative to the closure trigger 502 upon completion of a firing operation. It can be seen therefrom that the protrusion 602 on the firing trigger is completely pressed onto the button 603 of the closure trigger 502. At this time, the button makes a sound to indicate that a firing operation has been completed.

Figure 17:
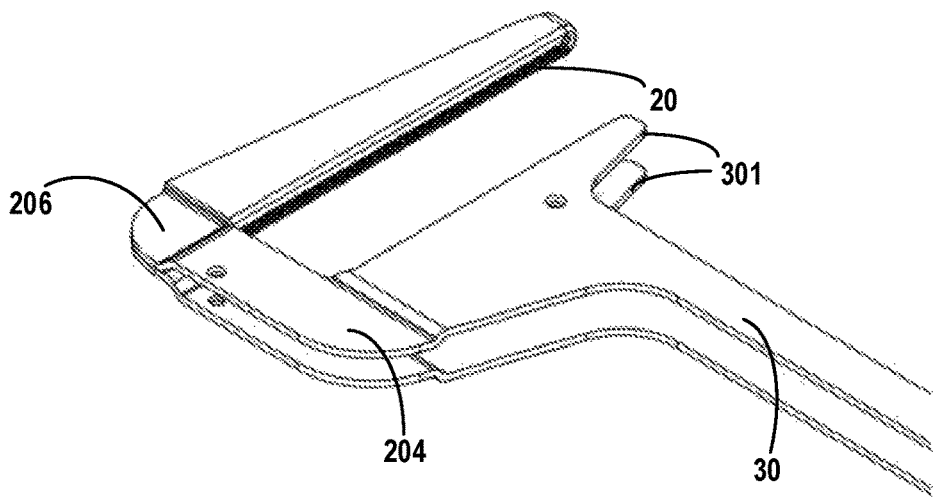
FIG. 17 is a partial perspective view of a distal end of a main body frame of a surgical stapler according to the present disclosure, where an anvil mounted on a hook plate is illustrated.

FIG. 17 is a partial perspective view of a main body frame of the surgical stapler at a distal end according to the present disclosure, where an anvil mounted on a hook plate is schematically illustrated. In FIG. 17 is shown a hook plate 204 for the surgical stapler that includes an anvil 20 varied in edge width and is used in cooperation with the anvil 20.

As shown therein, the anvil 20 of the surgical stapler according to the present disclosure is fixedly connected to the main body frame 30 of the stapler, and the main body frame typically consists of two support pieces 301 configured symmetrically. A slit is formed between the two support pieces 301. The firing bar 401 coupled to the closure and fire mechanism of the stapler can be received in the slit (not shown), and driven by the closure and fire mechanism, the staple cartridge 10 can be pushed towards the anvil 20 along the longitudinal direction of the stapler to implement staple firing. According to the present disclosure, a hook plate 204 is provided along the outside of the anvil 20. The hook plate 204 forms a bending portion 206 at an end of the anvil 20. The hook plate 204 is fixedly connected to the side of the anvil 20 by adhesion, riveting, welding or the like. In addition, the thickness of the hook plate 204 can be chosen as required actually, to obtain an anvil 20 varied in different edge width.

Figure 18:
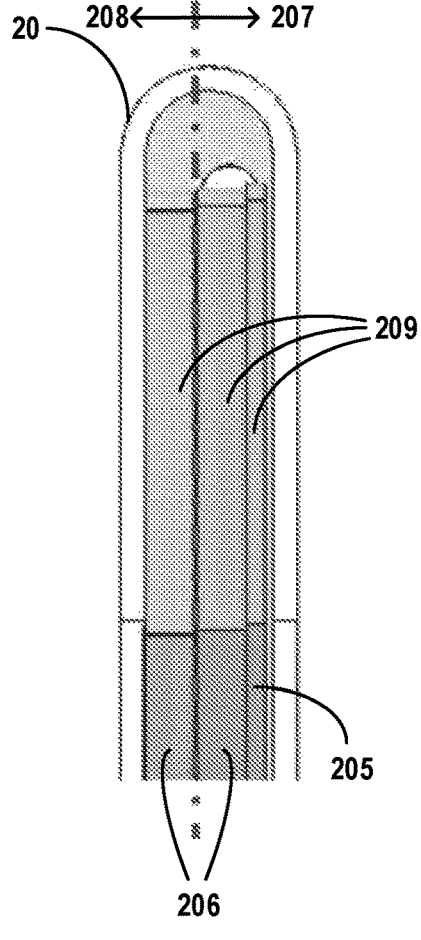
FIG. 18 is a schematic view of a dissected part of the anvil as shown in FIG. 17.

FIG. 18 is a main view schematically illustrating a truncated section at an end of an anvil 20 with a hook plate 204. The anvil 20 varied in edge width provides a support to the offset retaining pin assembly 102 of the surgical stapler. With the arrangement of an anvil 20 varied in edge width, the retaining pin receiving hole 203 is arranged offset from the longitudinal center axis of the anvil 20. In this way, a space-saving design is obtained, and the anvil 20 is structurally complete and of a suitable width. It is especially advantageous when a thick pin rod 121 is applied, which can ensure a good staple forming effect.

Referring further to FIG. 18, the anvil 20 includes a first portion 207 and a second portion 208 divided along the median plane of the surgical stapler, where the retaining pin receiving hole 203 is disposed on the first portion 207, and the width of the first portion 207 is greater than the width of the second portion 208. Moreover, the surgical stapler further includes an anvil mounting portion 209 on which the anvil 20 is fixedly mounted, where a thin inner shim 205 is disposed on a side surface of the anvil mounting portion 209 to offset a median plane of the anvil relative to a median plane of the surgical stapler. The shape of the inner shim 205 is identical to the shape of the side surface of the anvil mounting portion.

Preferred implementations according to the present disclosure have been described above with reference to the accompanied drawings. However, it would be appreciated by those skilled in the art that the accompanied drawings and corresponding description are provided merely for illustrating the objectives of the present disclosure, and on the basis, other various, substitutions or improvements are allowed, which all fall into the protection scope of the present disclosure.

LIST OF REFERENCE SIGNS 1 end effector of stapler
10 staple cartridge
20 anvil
30 main body frame of stapler
40 closure drive mechanism
60 indication mechanism
70 handle
101 cartridge body
102 retaining pin assembly
103 staple driver plate
111 tissue contact platform of cartridge body
112 staple cavity
113 hollow cavity
114 retaining pin hole
115 slot of cartridge body
116 ridge
117 staple cavity opening
121 pin rod
122 pin base
123 clip
124 clip
125 retaining pin tail
126 free end of retaining pin assembly
127 bump
131 avoidance feature
201 tissue contact surface of anvil
202 staple forming pocket
203 retaining pin receiving hole
204 hook plate
205 inner shim
206 bending portion of hook plate
207 first portion of anvil
208 second portion of anvil
209 anvil mounting portion
301 support piece of main body frame
401 firing bar
501 pistol grip
502 closure trigger
503 firing trigger
504 release button
505 shroud
601 indicator mark
602 protrusion
603 button
L longitudinal direction of staple cartridge and anvil
F longitudinal direction of stapler
R longitudinal direction of retaining pin assembly
We claim:

1. A staple cartridge for use with a surgical stapler, comprising:
a plurality of staples; and
a cartridge body, comprising:
a tissue contact platform,
a plurality of staple cavities, wherein each of the staple cavities comprises an opening formed in the tissue contact platform, the staples positioned in each of the staple cavities and being configured to extend out of the opening when deployed, and wherein the plurality of staple cavities are arranged in rows along a longitudinal direction of the staple cartridge, and
a retaining pin assembly slidably disposed in an end of the cartridge body proximate to the outside and operably connected to a closure drive mechanism of the surgical stapler, such that the retaining pin assembly is extendable distally out of a retaining pin hole opened on the tissue contact platform along a longitudinal direction of the surgical stapler when the closure drive mechanism is actuated, wherein the retaining pin assembly comprises a pin rod extending along a longitudinal direction of the retaining pin assembly, and the pin rod has a round cross section;
wherein, in the longitudinal direction of the staple cartridge, an outermost edge of an outermost staple cavity in at least one row of the staple cavities is aligned with or extends beyond a longitudinal axis of the pin rod; and
wherein the pin rod of the retaining pin assembly is either:
offset relative to a longitudinal centerline of the staple cartridge, or
centered relative to the longitudinal centerline of the staple cartridge while a longitudinal centerline of a plurality of rows of the staple cavities is offset relative to the longitudinal centerline of the staple cartridge.

2. The staple cartridge of claim 1, wherein the pin rod of the retaining pin assembly is offset relative to the longitudinal centerline of the staple cartridge, and the longitudinal centerline of the plurality of rows of the staple cavities coincides with the longitudinal centerline of the staple cartridge.

3. The staple cartridge of claim 1, wherein the pin rod of the retaining pin assembly is offset relative to the longitudinal centerline of the staple cartridge, and the longitudinal centerline of the plurality of rows of the staple cavities is offset relative to the longitudinal centerline of the staple cartridge.

4. The staple cartridge of claim 1, wherein the staple cavities are arranged in two rows, where an outermost edge of an outermost staple cavity in one of the two staple cavity rows extends beyond the longitudinal axis of the pin rod, and another staple cavity row is positioned adjacent to the retaining pin hole.

5. The staple cartridge of claim 1, wherein the pin rod comprises a free end that is extendable out of the retaining pin hole and the other end opposing the free end, and the retaining pin assembly further comprises: a pin base fixedly connected to the other end of the pin rod,
wherein the pin rod is offset relative to a longitudinal center axis of the pin base.

6. The staple cartridge of claim 5, wherein the retaining pin assembly has an asymmetric structure at two sides of the offset pin rod.

7. The staple cartridge of claim 5, further comprising: a staple driver plate extending along the longitudinal direction of the staple cartridge and provided, on a surface facing a distal end of the surgical stapler, with a plurality of teeth extending towards a distal end of the surgical stapler and configured to push the staples out of the staple cavities,
wherein the staple driver plate is formed at a distal end portion proximate to the retaining pin assembly with an avoidance feature that allows the retaining pin to advance towards the distal end of the surgical stapler by surpassing the staple driver plate.

8. The staple cartridge of claim 7, wherein the avoidance feature comprises a cutout formed at one side of the staple driver plate adjacent to the retaining pin assembly, the cutout extends along a firing direction of the staple cartridge, and is configured to allow the retaining pin to pass therethrough.

9. The staple cartridge of claim 5, wherein the retaining pin assembly further comprises clips formed at two sides of the pin base, and the clips are configured to extend out of the cartridge body along slots formed on two side surfaces of the cartridge body and extending along a firing direction of the staple cartridge, so that the retaining pin assembly is operable by a user to slide along the slot.

10. The staple cartridge of claim 9, wherein the clips have an ear-like structure.

11. The staple cartridge of claim 10, wherein the ear-like clips located at two sides of the pin base are different in size.

12. The staple cartridge of claim 1, wherein the cartridge body further comprises a plurality of ridges extending from the tissue contact platform, and wherein at least a part of each of the staple cavity openings is surrounded by portions of the ridges or a portion of a ridge.

13. The staple cartridge of claim 1, wherein a bump is formed around at least a part of the retaining pin hole.

14. The staple cartridge of claim 1, wherein a free end of the retaining pin assembly is configured as a tip.

15. The staple cartridge of claim 1, wherein the pin rod of the retaining pin assembly has a diameter greater than 1.7 mm.

16. A surgical stapler for stapling tissue in a surgical procedure, comprising:
    a staple cartridge according to claim 1;
    an anvil for forming staples in the staple cartridge; and
    a firing drive mechanism operably connected to the staple cartridge, the staple firing mechanism for actuating the staple driver plates to drive a plurality of staple drivers to move distally from the surgical stapler, so as to deploy the staples from the staple cavities, wherein the anvil comprises:
    a tissue contact surface,
    a plurality of staple forming pockets formed on the tissue contact surface, the staple forming pockets arranged in rows corresponding to a plurality of staple cavities of the staple cartridge, and
    a retaining pin receiving hole for receiving a free end of a retaining pin assembly of the staple cartridge, wherein the retaining pin receiving hole is arranged at an end of the anvil proximate to the outside,
    wherein, in a longitudinal direction of the anvil, an outermost edge of an outermost staple forming pocket in at least one row of the staple forming pockets is aligned with or extends beyond a center of the retaining pin receiving hole at the anvil side.

17. The surgical stapler of claim 16, wherein the retaining pin receiving hole at the anvil side is centered relative to a longitudinal centerline of the anvil, and a longitudinal centerline of a plurality of rows of the staple forming pockets is offset relative to the longitudinal centerline of the anvil.

18. The surgical stapler of claim 16, wherein the retaining pin receiving hole at the anvil side is offset relative to the longitudinal centerline of the anvil, and a longitudinal centerline of a plurality of rows of the staple forming pockets is offset relative to the longitudinal centerline of the anvil.

19. The surgical stapler of claim 18, wherein the anvil comprises a first portion and a second portion divided along a median plane of the surgical stapler, the retaining pin receiving hole at the anvil side being disposed on the first portion, and wherein a width of the first portion is greater than a width of the second portion.

20. The surgical stapler of claim 16, wherein the retaining pin receiving hole at the anvil side is offset relative to the longitudinal centerline of the anvil, and a longitudinal centerline of a plurality of rows of the staple forming pockets coincides with the longitudinal centerline of the anvil.

* * * * *